United States Patent
Howitz et al.

(10) Patent No.: US 9,637,773 B2
(45) Date of Patent: May 2, 2017

(54) COMPOUNDS AND METHODS FOR DETECTION OF ENZYMES THAT REMOVE FORMYL, SUCCINYL, METHYL SUCCINYL OR MYRISTOYL GROUPS FROM ε-AMINO LYSINE MOIETIES

(75) Inventors: Konrad T. Howitz, Allentown, PA (US); Zhongda Zhang, Wynnewood, PA (US); Anne Kisielewski, Wilmington, DE (US); Elizabeth Dale, Allentown, PA (US); Wayne Forrest Patton, Dix Hills, NY (US)

(73) Assignee: Enzo Life Sciences, Inc., Farmingdale, NY (US)

( * ) Notice: Subject to any disclaimer, the term of this patent is extended or adjusted under 35 U.S.C. 154(b) by 322 days.

(21) Appl. No.: 12/930,693

(22) Filed: Jan. 13, 2011

(65) Prior Publication Data
US 2012/0183948 A1    Jul. 19, 2012

(51) Int. Cl.
| | | |
|---|---|---|
| C07D 407/00 | (2006.01) |
| C07D 493/00 | (2006.01) |
| C07D 319/00 | (2006.01) |
| C07D 323/00 | (2006.01) |
| C07D 305/14 | (2006.01) |
| C07D 307/94 | (2006.01) |
| C07D 311/96 | (2006.01) |
| C07D 313/06 | (2006.01) |
| C07D 313/20 | (2006.01) |
| C07D 317/72 | (2006.01) |
| C07D 311/02 | (2006.01) |
| C12Q 1/34 | (2006.01) |
| C07D 311/16 | (2006.01) |
| C07D 493/10 | (2006.01) |

(52) U.S. Cl.
CPC .............. *C12Q 1/34* (2013.01); *C07D 311/16* (2013.01); *C07D 493/10* (2013.01)

(58) Field of Classification Search
CPC .......................... C07D 407/00; C07D 493/00
See application file for complete search history.

(56) References Cited

U.S. PATENT DOCUMENTS

| | | |
|---|---|---|
| 7,033,778 B2 | 4/2006 | Tamai et al. |
| 7,256,013 B2 | 8/2007 | Tamai et al. |
| 2006/0014705 A1 | 1/2006 | Howitz et al. |

FOREIGN PATENT DOCUMENTS

| | | | |
|---|---|---|---|
| WO | WO 97/27327 | * | 7/1997 |
| WO | WO 97/27327 A2 | * | 7/1997 |
| WO | WO 2006/130669 A2 | * | 7/2006 |
| WO | WO 2006/130669 A2 | * | 12/2006 |
| WO | WO2008/095296 | | 8/2008 |
| WO | WO 2008/095296 A1 | * | 8/2008 |
| WO | WO 2008/147949 A1 | * | 12/2008 |
| WO | WO2011/031330 | | 3/2011 |
| WO | WO2011/034623 | | 3/2011 |
| WO | WO 2012/088268 A2 | * | 6/2012 |

OTHER PUBLICATIONS

Jiang, T. et al. N-formylation of lysine in histone proteins as a secondary modification arising from oxidative DNA damage. PNAS. 2007, vol. 104, p. 61, figure 1.*
Carey, FA. Organic Chemistry 6th Ed. McGraw Hill. 2006, chapter 1, p. 9.*
Jiang, T. et al. N-formylation of lysine in histone proteins as a secondary modification arising from oxidative DNA damage. PNAS. 2007, vol. 104, p. 61.*
Kocienski, PJ. Protecting Groups. THIEME. 2005, p. 188, 488.*
Rademann, J. et al. Resin-Bound Aminofluorescein for C-Terminal Labeling of Peptides: High-Affinity Polarization Probes Binding to Polyproline-Specific GYF Domains. ChemBioChem. 2008, vol. 9, p. 2457.*
Grehn, L. et al. Removal of Formyl, Acetyl, and Benzoyl Groups from Amides with Conversion into the Corresponding t-butyl Carbamates. Chem. Comm. 1985, p. 1317.*
Mancini, JA. et al. Expression, Maturation, and Rhodamine-Based Fluorescence Assay of Human Cathepsin K Expressed in CHO Cells. Biochemical Pharmacology. 2000, vol. 60, p. 759.*
Mitsos, C. Isosteres in Medicinal Chemistry. Group Meeting Notes. Feb. 1, 2006, p. 1.*
Carey, FA. Organic Chemistry 6th Ed. McGraw Hill. 2006, p. 860.*
Bakhanashvili et al., p53 in mitochondria enhances the accuracy of DNA synthesis, Cell Death and Differentiation 2008,1865-1874, 15.
Benoiton et al., The hydrolysis of two epsilon-N-methyl-L-lysine derivatives by trypsin, Biochim. Biophys. Acta, 1966, 613-616, 113.
Bhalla, Kapil N., Epigenetic and Chromatin Modifiers As Targeted Therapy of Hematologic Malignancies, J Clin Oncol 2005, 3971-3993, 23.

(Continued)

Primary Examiner — Noble Jarrell
Assistant Examiner — Ben S Michelson
(74) Attorney, Agent, or Firm — Paul Diamond, Esq.

(57) ABSTRACT

Provided is a compound that comprises the structure:

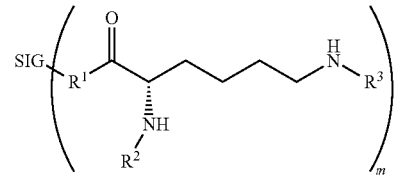

where SIG is a signaling molecule and $R^3$ is a formyl, a succinyl, a methyl succinyl, or a myristoyl. Also provided is a kit is provided that comprises the above compound, with instructions for determining the presence of the enzyme. Additionally, a method is provided for determining whether a sample has an enzyme that removes a succinyl, a methyl succinyl, a formyl, or a myristoyl moiety from an ε-amino of a lysine. Also provided is a method of determining whether a molecule inhibits an enzyme that removes a succinyl, a methyl succinyl, a formyl, or a myristoyl moiety from an ε-amino of a lysine.

5 Claims, 12 Drawing Sheets

(56) References Cited

OTHER PUBLICATIONS

Bitterman et al., Inhibition of Silencing and Accelerated Aging by Nicotinamide, a Putative Negative Regulator of Yeast Sir2 and Human SIRT1, The Journal of Biological Chemistry 2002, 45099-45107, 277.
Blander et al., The SIR2 family of protein deacetylases, Annu. Rev. Biochem. 2004, 417-35, 73.
Borra et al., Substrate Specificity and Kinetic Mechanism of the Sir2 Family of NAD+-Dependent Histone/Protein Deacetylases, Biochemistry 2004, 9877-9887, 43.
Bradner et al., Chemical Phylogenetics of Histone Deacetylases, Nat Chem Biol. 2010, 238-243, 6.
Brownlee et al., Nonenzymatic glycosylation reduces the susceptibility of fibrin to degradation by plasmin, Diabetes 1983, 680-684, 32.
Buck et al., Diversity in the Sir2 family of protein deacetylases, J. Leukoc. Biol. 2004, 939-950, 75.
Chen et al., The p53 Pathway Promotes Efficient Mitochondrial DNA Base Excision Repair in Colorectal Cancer Cells, Cancer Res 2006, 3485-3494, 66.
Cheng et al., Molecular Characterization of Propionyllysines in Non-histone Proteins, Molecular & Cellular Proteomics 2009, 45-52, 8.
Du et al., Investigating the ADP-ribosyltransferase Activity of Sirtuins with NAD Analogues and 32P-NAD, Biochemistry 2009, 2878-2890, 48.
Enzo Life Sciences, Inc., HDAC Fluorimetric Assay/Drug Discovery Kit, Instruction Manual BML-AK500, 2011.
Enzo Life Sciences, Inc., Fluor de Lys®-Green HDAC Assay Kit, Instruction Manual BML-AK530, 2011.
Enzo Life Sciences, Inc., SIRT1 Fluorometric Drug Discovery Kit, Instruction Manual BML-AK555, 2011.
Enzo Life Sciences, Inc., SIRT5 (human), (recombinant) (His-tag), BML-SE555, 2011.
Frye et al., Anti-sense oligonucleotides, for progestin receptors in the VMH and glutamic acid decarboxylase in the VTA, attenuate progesterone-induced lordosis in hamsters and rats, Behavioural Brain Research 2000, 55-64, 115.
Gertz et al., Function and regulation of the mitochondrial Sirtuin isoform Sirt5 in Mammalia, Biochimica et Biophysica Acta 2010, 1658-1665, 1804.
Haigis et al., SIRT4 Inhibits Glutamate Dehydrogenase and Opposes the Effects of Calorie Restriction in Pancreatic Beta Cells, Cell 2006, 941-954, 126.
Hodawadekar et al., Chemistry of acetyl transfer by histone modifying enzymes: structure, mechanism and implications for effector design, Oncogene 2007, 5528-5540, 26.
Hoffmann et al., A non-isotopic assay for histone deacetylase activity, Nucleic Acids Research, 1999, 2057-2058, 27.
Howitz et al., Small molecule activators of sirtuins extend *Saccharomyces cerevisiae* lifespan, Nature 2003, 191-196, 425.
Huang et al., Mitochondrial sirtuins, Biochimica et Biophysica Acta 2010, 1645-1651, 1804.
Imai et al., Transcriptional silencing and longevity protein Sir2 is an NAD-dependent histone deacetylase, Nature 2000, 795-800, 403.
Inglese et al., Assay guidance manual version 5.0, Eli Lilly & Co. and NIH Chemical Genomics Center, website 2011.
Jiang et al., N-formylation of lysine in histone proteins as a secondary modification arising from oxidative DNA damage, PNAS, 2007, 60-65,104.
Johnson et al., Monitoring of Relative Mitochondrial Membrane Potential in Living Cells by Fluorescence Microscopy, The Journal of Cell Biology 1981, 526-535, 88.
Joys et al., The susceptibility to tryptic hydrolysis of peptide bonds involving epsilon-N-methyllysine, Biochimica et Biophysica Acta 1979, 360-362, 581.
Kato et al., Detection of lipid-lysine amide-type adduct as a marker of PUFA oxidation and its applications, Archives of Biochemistry and Biophysics 2010, 182-187, 501.
Kawai et al., Formation of N epsilon-(succinyl)lysine in vivo: a novel marker for docosahexaenoic acid-derived protein modification, J. Lipid Res. 2006, 1386-1398, 47.
Kim et al., Substrate and Functional Diversity of Lysine Acetylation Revealed by a Proteomics Survey, Molecular Cell 2006, 607-618, 23.
Langley et al., Human SIR2 deacetylates p53 and antagonizes PML/p53-induced cellular senescence, The EMBO Journal 2002, pp. 2383-2396, 21.
Liszt et al., Mouse Sir2 Homolog SIRT6 Is a Nuclear ADP-ribosyltransferase, The Journal of Biological Chemistry 2005, 21313-21320, 280.
Liu et al., Fluorescent molecular probes v: a sensitive caspase-3 substrate for fluorometric assays, Bioorganic & Medicinal Chemistry Letters 1999, 3231-3236, 9.
Luo et al., Negative Control of p53 by Sir2 alpha Promotes Cell Survival under Stress, Cell, 2001, 137-148, 107.
Mahlknecht et al., Assignment of the NAD-dependent deacetylase sirtuin 5 gene (SIRT5) to human chromosome band 6p23 by in situ hybridization, Cytogenet Genome Res 2006, 208-212, 112.
Mahyar-Roemer et al., Mitochondrial p53 levels parallel total p53 levels independent of stress response in human colorectal carcinoma and glioblastoma cells, Oncogene 2004, 6226-6236, 23.
Martinez et al., Effect of Proteolytic Enzymes on Bacterial Flagella, Journal of Bacteriology, 1972, 1239-1246, 109.
Michishita et al., Evolutionarily Conserved and Nonconserved Cellular Localizations and Functions of Human SIRT Proteins, Molecular Biology of the Cell 2005, 4623-4635, 16.
Nakagawa et al., SIRT5 Deacetylates Carbamoyl Phosphate Synthetase 1 and Regulates the Urea Cycle, Cell 2009, 560-570, 137.
Nakamura et al., Localization of mouse mitochondrial SIRT proteins: Shift of SIRT3 to nucleus by co-expression with SIRT5, Biochemical and Biophysical Research Communications 2008, 174-179, 366.
North et al., Preparation of enzymatically active recombinant class III protein deacetylases, Methods 2005, 338-345, 36.
North et al., The Human Sir2 Ortholog, SIRT2, Is an NAD+-Dependent Tubulin Deacetylase, Molecular Cell, 2003 437-444, 11.
Pantazis et al., Quantitative Determination of Histone Modification, The Journal of Biological Chemistry 1981, 4669-4675, 256.
Pfister et al., Opposing Effects of Sirtuins on Neuronal Survival: SIRT1—Mediated Neuroprotection Is Independent of Its Deacetylase Activity, PLoS One 2008, e4090, 3.
Poncz et al., The Resistance to Tryptic Hydrolysis of Peptide Bonds Adjacent to N epsilon, N-Dimethyllysyl Residues, The Journal of Biological Chemistry, 1983,1844-1850, 258.
Rusche et al., The establishment, inheritance, and function of silenced chromatin in *Saccharomyces cerevisiae*, Annu. Rev. Biochem. 2003, 481-516, 72.
Schlicker et al., Substrates and Regulation Mechanisms for the Human Mitochondrial Sirtuins Sirt3 and Sirt5, J. Mol. Biol. 2008, 790-801, 382.
Schuetz et al., Structural Basis of Inhibition of the Human NAD+-Dependent Deacetylase SIRT5 by Suramin, Structure 2007, 377-389,15.
Schultz et al., Kinetics and Comparative Reactivity of Human Class I and Class IIb Histone Deacetylases, Biochemistry 2004,11083-11091, 43.
Schwer et al., Calorie restriction alters mitochondrial protein acetylation, Aging Cell 2009, 604-606, 8.
Seely et al., Effect of Methylation and chain length on kinetic constants of trypsin substrates. epsilon-N-Methyllysine and homolysine derivatives as substrates, Can. J. Biochem. 1970, 1122-1131, 48.
Shimazu et al., Acetate metabolism and aging: An emerging connection, Mechanisms of Ageing and Development 2010, 511-516, 131.

(56) References Cited

OTHER PUBLICATIONS

Smith et al., A phylogenetically conserved NAD+-dependent protein deacetylase activity in the Sir2 protein family, PNAS 2000, 6658-6663, 97.

Souza-Pinto et al., p53 functions in the incorporation step in DNA base excision repair in mouse liver mitochondria, Oncogene 2004, 6559-6568, 23.

Starai et al., Sir2-Dependent Activation of Acetyl-CoA Synthetase by Deacetylation of Active Lysine, Science, 2002, 2390-2392, 298.

Stein, Wilfred D., Transport and diffusion across cell membranes, Academic Press Inc., 1986, 69-112.

Stevenson et al., Myristyl Acylation of the Tumor Necrosis Factor Alpha Precursor on Specific Lysine Residues, The Journal of Experimental Medicine 1992, 1053-1062, 176.

Stevenson et al., The 31-kDa precursor of interleukin I alpha is myristoylated on specific lysines within the 16-kDa N-terminal propiece, Proc. Natl. Acad. Sci. USA 1993, 7245-7249, 90.

Tanner et al., Silent information regulator 2 family of NAD-dependent histone/protein deacetylases generates a unique product, 1-O-acetyl-ADP-ribose, PNAS 2000, 14178-14182, 97.

Tanny et al., Coupling of histone deacetylation to NAD breakdown by the yeast silencing protein Sir2: Evidence for acetyl transfer from substrate to an NAD breakdown product, PNAS 2001, 415-420, 98.

Vaziri et al., hSIR2SIRT1 Functions as an NAD-Dependent p53 Deacetylase, Cell, 2001, 149-159, 107.

Watkins et al., Evidence for 26 distinct acyl-coenzyme A synthetase genes in the human genome, J. Lipid Res. 2007, 2736-2750, 48.

Wisniewski et al., Mass Spectrometric Mapping of Linker Histone H1 Variants Reveals Multiple Acetylations, Methylations, and Phosphorylation as Well as Differences between Cell Culture and Tissue, Molecular & Cellular Proteomics 2007, 72-87, 6.

Wisniewski et al., N epsilon-Formylation of lysine is a widespread post-translational modification of nuclear proteins occurring at residues involved in regulation of chromatin function, Nucleic Acids Research, 2008, 570-577, 36.

Zhang et al., A Simple Statistical Parameter for Use in Evaluation and Validation of High Throughput Screening Assays, J Biomol Screen 1999, 67-73, 4.

Zhao et al., Structure and Substrate Binding Properties of cobB, a Sir2 Homolog Protein Deacetylase from *Escherichia coli*, J. Mol. Biol. 2004, 731-741, 337.

Zhou et al., Cloning and characterization of a histone deacetylase, HDAC9, PNAS 2001, 10572-10577, 98.

Du et al., Sirt5 is a NAD-dependent protein lysine demalonylase and desuccinylase, Science 2011, 806-809, 334.

Zhang et al., Identification of lysine succinylation as a new post-translational modification, Nature Chemical Biology 2011, 58-63, 7.

Copeland, R.A., *Enzymes: A Practical Introduction to Structure, Mechanism, and Data Analysis,* Wiley-VCH, NY $2^{nd}$ ed. (2000).

De Sousa Pinto et al., "p53 functions in the incorporation step in DNA base excision repair in mouse liver mitochondria," *Oncogene,* vol. 23, pp. 6559-6568 (2004).

Lin, H., "The Enzymatic Activity of Sirtuins: Beyond NAD-Dependent Deacetylation," Chemical Biology Discussion Group Seminar, New York Academy of Sciences (2010)—Abstract Only.

Shimazu, et al., "Acetate metabolism and aging: An emerging connection," *Mech. Ageing Dev.,* vol. 131, pp. 511-516 (2010).

\* cited by examiner

COMPOUNDS AND METHODS FOR DETECTION OF ENZYMES THAT REMOVE FORMYL, SUCCINYL, METHYL SUCCINYL OR MYRISTOYL GROUPS FROM ε-AMINO LYSINE MOIETIES

BACKGROUND OF THE INVENTION (1) Field of the Invention

The present application generally relates to reagents for detecting enzymes. More specifically, substrates for detecting various enzymes that remove modifications of ε-amino moieties are provided.

(2) Description of the Related Art

Most sirtuin enzymes, also known as class III histone deactylases (class III HDACs), catalyze a reaction which couples deacetylation of protein ε-acetyllysine residues to the formation of O-acetyl-ADP-ribose and nicotinamide from $NAD^+$ (Imai et al., 2000; Tanner et al., 2000; Tanny and Moazed, 2001). Some sirtuins, notably human sirtuins SIRT4 and SIRT6, catalyze an alternative reaction, the transfer of an ADP-ribosyl group from $NAD^+$ to proteins (Liszt et al., 2005; Haigis et al., 2006), although the physiological relevance of these reactions is in question (Du et al., 2009). Sirtuin homologs are found in all forms of life, including the archaea, the bacteria, and both unicellular and multicellular eukaryotes (Smith et al., 2000; Blander and Guarente, 2004; Buck et al., 2004; Frye, 2000). The founding exemplar of the group, Sir2 from baker's yeast (Saccharomyces cerevisiae), was named for its role in gene-silencing (Silent information regulator 2; Rusche et al., 2003). Transcriptional silencing by Sir2 is linked to its deacetylation of lysines in the N-terminal tails of the histones in chromatin, hence the classification as a class III HDAC. Lysine deacetylation by sirtuins, however, extends beyond histones. Targets of sirtuin regulatory deacetylation include mammalian transcription factors such as p53 (Luo et al., 2001; Vaziri et al., 2001; Langley et al., 2002), the cytoskeletal protein tubulin (North et al., 2003), and the bacterial enzyme acetyl-CoA synthetase (Starai et al., 2002; Zhao et al., 2004) and its mammalian homologs (Shimazu et al., 2010).

SIRT5, along with two other mammalian sirtuins, SIRT3 and SIRT4, is localized to the mitochondria (Michishita et al., 2005; Nakagawa et al., 2009). The human SIRT5 gene is located in a chromosomal region in which abnormalities are associated with malignancies, suggesting a possible SIRT5 role in cancer (Mahlknecht et al., 2008). Thus far, the best studied of SIRT5's possible physiological roles is the deacetylation and enhancement of the activity of the mitochondrial matrix enzyme carbamoyl phosphate synthase 1 (CPS1), the rate-limiting enzyme for urea synthesis in the urea cycle (Nakagawa et al., 2009). Increased urea synthesis is required for removal of nitrogenous waste (ammonia) during periods of increased amino acid catabolism, including calorie restriction, fasting and the consumption of a high protein diet. Under these conditions, SIRT5 deacetylation of CPS1 is increased, along with CPS1 activity (Nakagawa et al., 2009). At least in the instance of starvation, the increased SIRT5 activity may be attributed to increased levels of the sirtuin co-substrate $NAD^+$ in the mitochondria, which in turn is due to induction of the $NAD^+$ synthetic pathway enzyme nicotinamide phosphoribosyltransferase, (Nampt) (Nakagawa et al., 2009). It should be noted, however, that two proteomic studies of the mouse mitochondrial "acetylome" are in possible conflict with the CPS1 results of Nakagawa et al. (2009). One group observed that calorie restriction increased acetylation at 7 of 24 sites in CPS1, but did not lead to deacetylation at any sites (Schwer et al., 2009). A comparison of the acetylated proteins of fed and fasted mice found that fasting induced the addition of 4 acetylated sites to CPS1, while only one of five sites present in the fed condition disappeared upon fasting (Kim, S. C. et al., 2006).

The evidence for another possible SIRT5 acetylated substrate, cytochrome c, is also equivocal (Huang et al., 2010; Gertz and Steegborn, 2010). While SIRT5 has been shown to deacetylate cytochrome c in vitro (Schlicker et al., 2008), there is conflicting data regarding whether it can localize to the same sub-mitochondrial compartment as cytochrome c, the intermembrane space (Schlicker et al., 2008; Nakamura et al., 2008; Nakagawa et al., 2009). Cytochrome c is a component of the respiratory electron transport chain and release of cytochrome c from the mitochondrial intermembrane space to the cytoplasm promotes apoptosis (programmed cell death). Overexpression of SIRT5 in cerebellar granule neurons is pro-apoptotic, consistent at least with a possible SIRT5 regulatory role in the latter of these two processes, apoptosis (Pfister et al., 2008). A regulatory SIRT5 role in respiration has also been suggested (Gertz and Steegborn, 2010).

An alternative view of SIRT5's physiological function is that it may primarily involve catalysis of reactions other than deacetylation. SIRT5's deacetylase activity is detectable but weak with an acetylated histone H4 peptide (North et al., 2005) and with chemically acetylated histones or bovine serum albumin (Schuetz et al., 2007). The catalytic efficiency of SIRT5 with an acetylated histone H3 peptide ($k_{cat}/K_m$=3.5 $s^{-1}$ $M^{-1}$) is orders of magnitude lower than several human and yeast sirtuins (SIRT1, SIRT2, Sir2, Hst2) and more than 20-fold lower than the next weakest deacetylase tested, human SIRT3 (Du et al., 2009). Although there is a seeming conflict between the idea of SIRT5 as a non-deacetylase and its effects on CPS1, it should be noted that the rate of SIRT5 deacetylation of CPS1 has not been quantified; the deacetylation was only shown in qualitative way by western blotting with anti-acetyllysine (Nakagawa et al., 2009). Further, although SIRT5 performs an $NAD^+$-dependent activation of CPS1 and an $NAD^+$-dependent deacetylation of CPS1, no mechanistic link between the deacetylation and the activation has been established. The in vitro SIRT5/CPS1 activation experiments were performed with crude mitochondrial matrix lysates from SIRT5 knock-out mice serving as the CPS1 source (Nakagawa et al., 2009). Conceivably, the CPS1 harbored another modification, in addition to acetylation, that SIRT5 reversed in an $NAD^+$-dependent reaction. Consistent with this possibility is recently presented evidence that mitochondrial proteins are lysine-succinylated and that SIRT5 can desuccinylate peptides with efficiencies similar to the deacetylation efficiencies of human SIRTs 1-3 (Lin, 2010).

The activity of lysine deacetylases (class I and II HDACs and sirtuins (class III HDACs)) can be conveniently measured with synthetic substrates of the general structure X-Lysine(ε-acetyl)-F, where F is a fluorophore or other moiety for which a measurable signal increases after cleavage of its direct covalent bond to the carboxyl of lysine and X may be an N-terminal blocking group such as acetyl (Ac) or a peptide sequence (for single-lysine substrates see Hoffman et al., 1999; Enzo Life Sciences Instruction Manual for BML-AK500; Zhou et al., 2001; Bitterman et al., 2002). For longer peptide substrates see U.S. Pat. No. 7,033,778; U.S. Pat. No. 7,256,013; Howitz et al., 2003. A signal proportional to deacetylation is generated by virtue of the fact that trypsin, among other lysyl-specific peptidases, will not cleave amide bonds on the carboxyl side of lysine if the ε-amino of the lysine side-chain is modified by an acetyl function (Pantazis and Bonner, 1981; Brownlee et al., 1983). A homogenous, endpoint deacetylase assay can thus consist of a two-step procedure in which the deacetylase is first allowed to act on the substrate and signal is then generated in a second step in which trypsin selectively cleaves the deacetylated substrate molecules. A continuously coupled version of this assay procedure has been described in which the deacetylase, the substrate, and trypsin are all present in same reaction mixture during the deacetylation reaction (Schultz et al., 2004). It should be noted that not all modifications of the lysine ε-amino function result in elimination of trypsin cleavability at the lysine carboxyl. Trypsin will cleave at a reduced but significant rate at $N^\epsilon$-monomethyllysine residues (Benoiton and Deneault, 1966; Seely and Benoiton, 1970; Martinez et al., 1972; Joys and Kim, 1979), while $N^\epsilon,N^\epsilon$-dimethyllysine residues are resistant to trypsin cleavage (Poncz and Dearborn, 1983).

Although "X-Lysine(ε-acetyl)-F" substrates are widely used for the assay of various HDAC and sirtuin isoforms, assay of SIRT5 has been problematic because the efficiency of SIRT5 deacetylation of such substrates is extremely poor. For example, it has been asserted that SIRT5 "does not" deacetylate the p53 peptide substrate Ac-Arg-His-Lys-Lys (ε-acetyl)-AMC (Nakagawa et al., 2009). While SIRT5 will in fact deacetylate this peptide, significant levels of deacetylation require either a combination of high peptide substrate concentration (e.g. 500 μM), high concentration of the cosubstrate $NAD^+$ (1 to 5 mM) and large quantities of enzyme (~5 μg/50 μl assay=~3 μM SIRT5) (U.S. Patent Application Publication 20060014705) or the addition of a sirtuin activator such as resveratrol (Id.). Such conditions present severe practical problems for SIRT5 assays, particularly in drug discovery applications such as the screening of chemical libraries for SIRT5 inhibitor or activator "lead compounds" and the subsequent rounds of inhibitor/activator structure-activity relationship (SAR) characterization and chemical synthetic compound improvement. For example, high concentrations of the "X-Lysine(ε-acetyl)-F" type fluorogenic substrates produce a high background fluorescence in all samples. High fluorescence background increases the difficulty of observing statistically significant differences among positive controls, negative controls and inhibitor/activator "hits" (Zhang et al., 1999). Further, the lower limit for determining an enzyme inhibitor's $IC_{50}$ (concentration at which the inhibitor lowers enzyme activity to 50% of the uninhibited control sample) is ½ the enzyme concentration (Copeland, 2000; Inglese et al., 2008). Thus, the use of a high enzyme concentrations in an assay impedes the ability to quantitatively distinguish high and low potency inhibitors/activators and consequently interferes with chemical synthetic efforts to optimize pharmaceutical lead compounds.

The present invention provides compositions and methods which solve these problems for SIRT5 by, for example, enabling assays to be performed at drastically lower enzyme concentrations (≤20 ng/50 μl, ≤12 nM) and at lower fluorogenic substrate concentrations (≤50 μM), which produce lower fluorescent background levels. Substrates for detecting other enzymes that remove modifications of ε-amino moieties are also provided.

BRIEF SUMMARY OF THE INVENTION

Provided herein are compounds and methods useful for detecting enzymes that remove formyl, succinyl, methyl succinyl, or myristoyl moieties from ε-amino lysine moieties of proteins. In some embodiments, a compound is provided that comprises the structure:

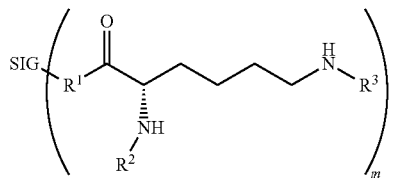

wherein SIG is a signaling molecule; m is an integer from 1 to about 10; $R^1$ is NH, O, S or $SO_2$; $R^2$ is a hydrogen, a halogen, an isothiocyano group (SNC), a sulfonate group ($SO_3R^4$), a sulfate group ($OSO_3R^4$), a carboxyl group ($CO_2H$), a carbonyl group ($COR^4$), an amido group ($CONR^4{}_2$ or $NR^3COR^4$), a carbamate group ($NR^4CO_2R^4$), a phosphate group ($OPO_3R^4{}_3$), a phosphonate group ($PO_3R^4{}_2$), an amino group ($NR^4{}_2$), an alkoxy group ($OR^4$), a thiol group ($SR^4$), a sulfoxy group ($SOR^4$), a sulfone group ($SO_2R^4$), a sulfonamide group ($SO_2NR^4{}_2$), a phosphino group ($PR^4{}_2$), a silane group ($SiR^4{}_3$), an oligopeptide sequence of 1-20 modified or unmodified amino acids or amino acid substitutes, a protein, a glycoprotein or a lipoprotein; each $R^4$ is independently a hydrogen, 1 to 3 halogen atoms, a substituted or unsubstituted $C_1$-$C_{10}$ straight-chain, branched or cyclic alkyl, alkenyl or alkynyl group wherein one or more C, CH or $CH_2$ groups may be substituted with an O atom, N atom, S atom, or NH group, an unsubstituted or substituted aromatic group wherein one or more C, CH or $CH_2$ groups may be substituted with an O atom, N atom, S atom, or NH group; and $R^3$ is a formyl, a succinyl, a methyl succinyl, or a myristoyl.

In other embodiments, a kit is provided that comprises the above compound, with instructions for determining the presence of the enzyme.

In further embodiments, a method is provided for determining whether a sample has an enzyme that removes a moiety from an ε-amino of a lysine, wherein the moiety is a succinyl, a methyl succinyl, a formyl, or a myristoyl. The method comprises (a) combining the sample with the above compound to make a sample-compound mixture, wherein $R^3$ of the compound is the moiety; (b) incubating the sample-compound mixture under conditions and for a time sufficient to allow the enzyme to remove the $R^3$; and (c) determining whether the $R^3$ is removed from the compound. In these methods, removal of $R^3$ from the compound indicates that the sample has the enzyme.

Additionally provided is a method of determining whether a molecule inhibits an enzyme that removes a moiety from an ε-amino of a lysine, wherein the moiety is a succinyl, a methyl succinyl, a formyl, or a myristoyl. The method comprises (a) combining the enzyme and the molecule with the above compound to make an enzyme-molecule-compound mixture, wherein $R^3$ of the compound is the moiety; (b) incubating the enzyme-molecule-compound mixture under conditions and for a time sufficient for the enzyme to remove the moiety in the absence of the molecule; and (c) determining whether the $R^3$ is removed from the compound to an equivalent degree that $R^3$ would be removed from the compound in the absence of the molecule. In these methods, the failure of the removal of $R^3$ from the compound to an equivalent degree as in the absence of the molecule indicates that the molecule is an inhibitor of the enzyme.

DETAILED DESCRIPTION OF THE INVENTION

Figure 1:
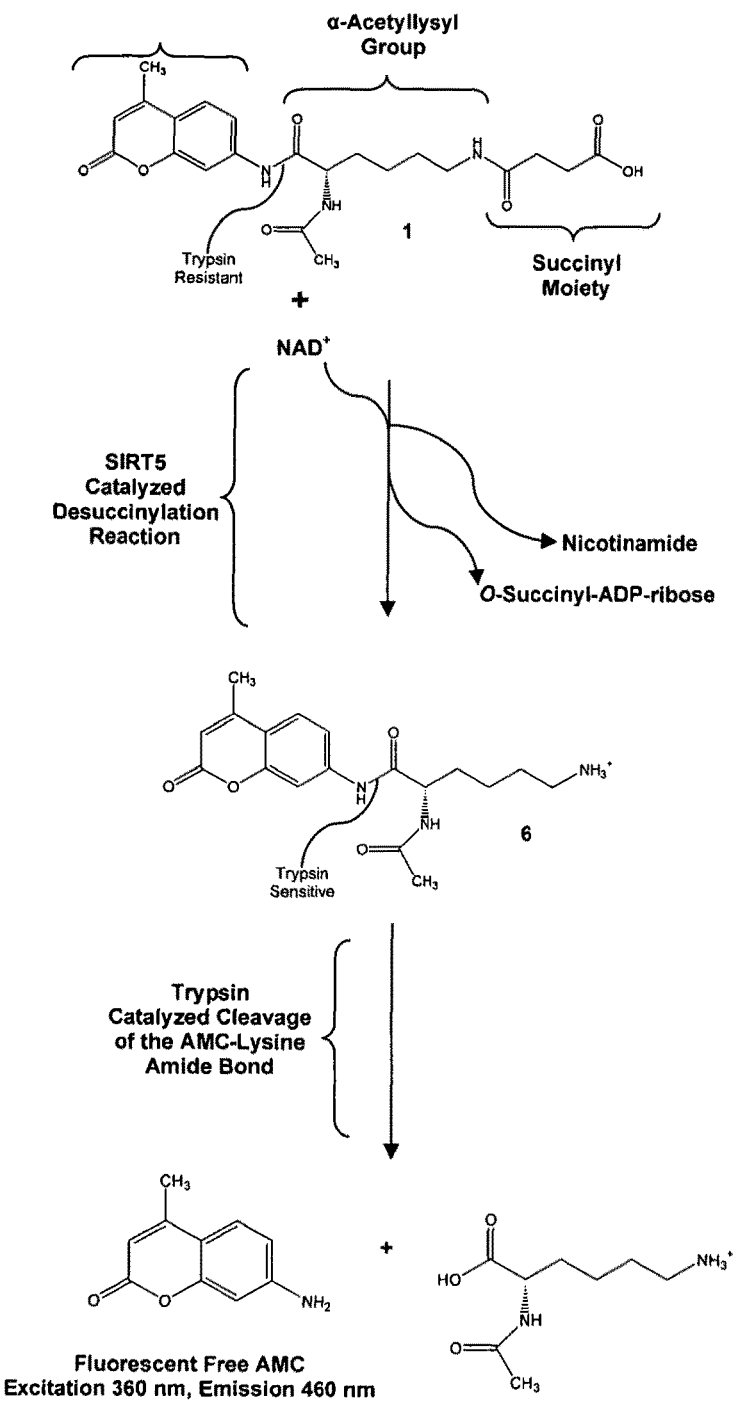
FIG. 1 is a reaction schematic for NAD$^+$-Dependent SIRT5 desuccinylation of the substrate N-(α-acetyl-Lysine (ε-succinyl))-AMC (Compound 1) and its detection by specific trypsin release of AMC from the desuccinylated product N-(α-acetyl-Lysine)-AMC (Compound 3).

As used herein, the singular forms "a", "an" and "the" are intended to include the plural forms as well, unless the context clearly indicates otherwise. Additionally, the use of "or" is intended to include "and/or", unless the context clearly indicates otherwise.

The present invention is directed to compounds and methods useful for detecting enzymes that remove formyl, succinyl, methyl succinyl, or myristoyl moieties from ε-amino lysine moieties of proteins. Methods for identifying inhibitors of those enzymes are also provided.

Thus, in some embodiments, a compound is provided that comprises the structure:

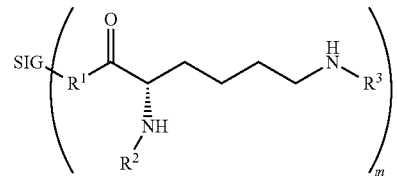

wherein
SIG is a signaling molecule;
m is an integer from 1 to about 10;
$R^1$ is NH, O, S or $SO_2$;
$R^2$ is a hydrogen, a halogen, an isothiocyano group (SNC), a sulfonate group ($SO_3R^4$), a sulfate group ($OSO_3R^4$), a carboxyl group ($CO_2H$), a carbonyl group ($COR^4$), an amido group ($CONR^4_2$ or $NR^3COR^4$), a carbamate group ($NR^4CO_2R^4$), a phosphate group ($OPO_3R^4_3$), a phosphonate group ($PO_3R^4_2$), an amino group ($NR^4_2$), an alkoxy group ($OR^4$), a thiol group ($SR^4$), a sulfoxy group ($SOR^4$), a sulfone group ($SO_2R^4$), a sulfonamide group ($SO_2NR^4_2$), a phosphino group ($PR^4_2$), a silane group ($SiR^4_3$), an oligopeptide sequence of 1-20 modified or unmodified amino acids or amino acid substitutes, a protein, a glycoprotein or a lipoprotein;
each $R^4$ is independently a hydrogen, 1 to 3 halogen atoms, a substituted or unsubstituted $C_1$-$C_{10}$ straight-chain, branched or cyclic alkyl, alkenyl or alkynyl group wherein one or more C, CH or $CH_2$ groups may be substituted with an O atom, N atom, S atom, or NH group, an unsubstituted or substituted aromatic group wherein one or more C, CH or $CH_2$ groups may be substituted with an O atom, N atom, S atom, or NH group; and
$R^3$ is a formyl, a succinyl, a methyl succinyl, or a myristoyl.

When the above compound is combined with an enzyme that removes the $R^3$ moiety under the proper conditions (e.g., in the presence of NAD⁺ when the enzyme is a class III HDAC [sirtuin]), the enzyme will remove the $R^3$ moiety, leaving an unaltered lysine residue. The resulting compound can be identified by any method known in the art, for example by mass spectroscopy, an immunoassay with an antibody that can distinguish between the compound with the $R^3$ group and without it, or an appropriate chromatographic method. In some embodiments, the compound without the $R^3$ group is a substrate for a peptidase while the compound with the $R^3$ group is not a peptidase substrate, such that removal of the $R^3$ group followed by treatment with the peptidase leaves SIG-$R^1$. In various embodiments, such as where SIG is a fluorescent or a luminescent moiety, SIG-$R^1$ has an increased signal (e.g., increased fluorescence or luminescence) than the intact compound. Under those conditions, the removal of the $R^3$ group is detected by addition of the peptidase, releasing SIG-$R^1$ and providing an increased signal. This increased signal thus establishes the presence of the enzyme that removes the $R^3$ group.

Thus, in some embodiments, the compound is a substrate for an enzyme such that the enzyme cleaves $R^3$ from the compound allowing a peptidase to cleave the resulting molecule between the $R^1$ and the CO moieties, such that SIG generates an increased signal relative to the signal generated with the compound. In these embodiments, the peptidase cannot cleave the compound comprising $R^3$. See Example.

The peptidase for these embodiments can be any peptidase that is capable of cleaving the compound without the $R^3$ group to release SIG-$R^1$ but not capable of cleaving the compound with the $R^3$ group. A nonlimiting example of such a peptidase, where the $R^3$ group is a succinyl, a methyl succinyl, or a myristoyl group, is trypsin.

Where the $R^3$ group is a formyl group, trypsin cannot be used as described for the other $R^3$ groups, since trypsin is capable of cleaving the compound between the $R^1$ and CO moieties even when the formyl group is not removed, albeit at a slower rate. See Benoiton and Deneault (1966), Seely and Benoiton (1970); Martinez et al. (1972); and Joys and Kim (1979). Under those circumstances, the use of trypsin would have to be modified such that the trypsin concentration is low enough such that the cleavage kinetics could be observed, where faster cleavage would indicate the elimination of the formyl $R^3$ group and slower cleavage would indicate the retention of the formyl $R^3$ group. Alternatively, another peptidase could be used when the $R^3$ group is a formyl group, e.g., a peptidase that will not cleave the compound between the $R^1$ and CO moieties when the formyl is present but will when the formyl is cleaved. A likely example of such an enzyme is endoproteinase Lys-C, which is unable to cleave monomethyllysine residues in proteins.

In some embodiments of these compounds, $R^1$ is NH. In other embodiments, m is 1 or 2.

In various embodiments, the $R^2$ moiety is a chemical protecting group. Such a protecting group is useful for the synthesis of the compound, since blocking the α-amino group allows the unambiguous addition of the $R^3$ moiety to the ε-amino group, without concern that the $R^3$ moiety would be inadvertently added to the α-amino group. Any protecting group known in the art as useful for protecting amino moieties could be useful here. Nonlimiting examples include FMOC, acetyl, benzoyl, Aloc, arysulfenyl, benzyl, BOM, BOC, carbobenzyloxy, diphenylmethylene, DMPM, EE, PMB, methoxycarbonyl, MeOZ, MoM, PMP, Noc, Nosyl, Nps, PhFl, Psec, pixyl, tosyl, Tsoc, Troc, trifluoroacetyl, TIPS, TMS, SES, Teoc, SEM, and Trityk. In some embodiments (as in the Example) $R^2$ is an acetyl group.

Examples of the compounds include

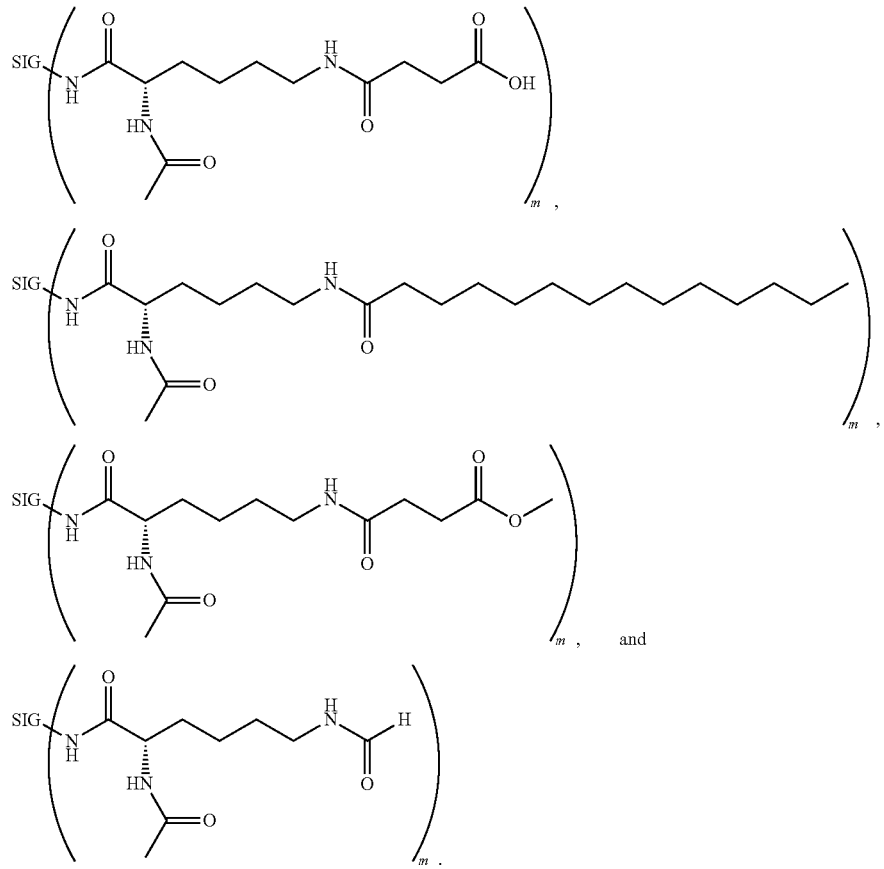

In various embodiments, m is 1 or 2.

These compounds are useful for detecting any enzyme that removes the $R^3$ group. In some embodiments, the enzyme is a histone deacetylase (HDAC). As shown in Table 2 below, HDAC2 and HDAC3/NCOR1 complex have some activity removing the $R^3$ moiety when that moiety is a succinyl group. Additionally, as shown in Table 3 below, HDAC1, HDAC3, and particularly HDAC2 and HDAC3/NCOR1 complex have activity removing the $R^3$ moiety when that moiety is a myristoyl or a methyl succinyl group. Additionally, HDAC9 has activity removing a methyl succinyl $R^3$ group.

In some of these embodiments, the HDAC is a sirtuin (a class III HDAC). As shown in Table 3 below, SIRT1, SIRT3 and SIRT6 have activity removing a myristoyl $R^3$ group. Additionally, as discussed extensively in the Example and shown in Table 2, SIRT5 has activity removing a succinyl $R^3$ group that is about two orders of magnitude greater than its deacetylase activity.

The signal, SIG, can be any chemical compound that has decreased fluorescence, luminescence or color intensity when functionalized with one or more of the

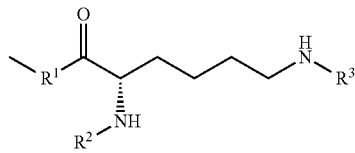

groups. Ideally, SIG is non-fluorescent, non-luminescent and colorless when the group is attached and intensely fluorescent, luminescent or colored when the group is removed. Additionally, SIG should contain or should be readily modified to contain reactive functionalities, as further discussed below, to which the above group could be attached to form a probe.

The invention is not narrowly limited to the use of any particular SIG. In various embodiments, SIG is a chromophore, a fluorophore, a luminescent moiety, an enzyme, a catalytic antibody, a ribozyme or a pro-enzyme.

In some embodiments, SIG is a fluorophore. Any fluorophore now known or later discovered can be utilized in these compounds. Examples of useful fluorophores include without limitation a symmetric or asymmetric cyanine dye, a merocyanine dye, a styryl dye, an oxazine dye, a xanthene dye, a coumarin dye or an iminocoumarin dye.

One class of the signal molecule, SIG, useful in the invention has a xanthene backbone shown in Scheme I below. The structures include both classical xanthene dyes and their lactone forms (Structures A and B, respectively) as well as aphenylic counterparts, which have their appended phenyl ring missing (Structures C).

Scheme I

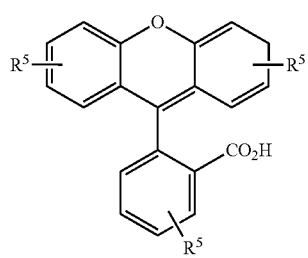
(A)

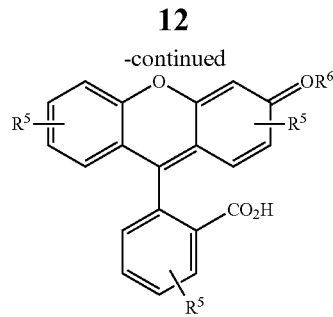
(B)

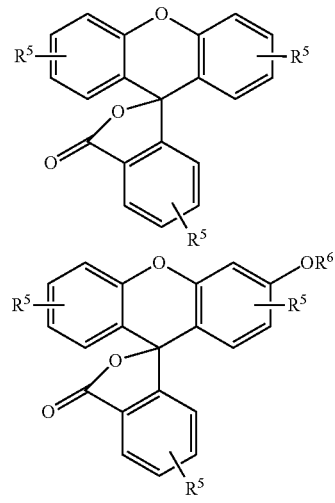
(C)

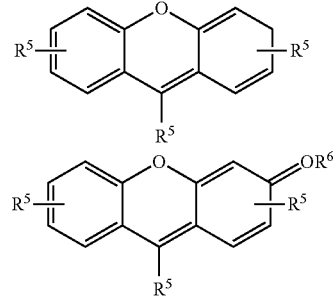

The substituent $R^5$ in Scheme I represents a variety of functionalities where at least one $R^5$ is a reactive group, which allows the attachment of the

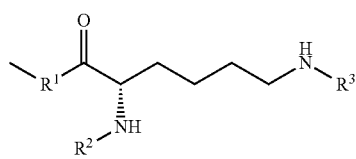

group and, if desired, at least one other $R^5$ is a reactive group, which allows the attachment of a protecting group to prevent attachment of additional groups, if preferred. The $R^5$s may be structurally the same or different and there may be several of them per ring. Also, some of the rings may not have any $R^5$s attached. Suitable examples of $R^5$ include, but are not limited to hydrogen, a halogen (F, Cl, Br, I), a nitro group ($NO_2$), a nitroso group (NO), a hydroxylamino group (NHOH), a cyano group (CN), an isocyano group (NC), a thiocyano group (SCN), an isothiocyano group (SNC), an azido group ($N_3$), a trihalomethyl group ($CX_3$, where X is a halogen), a sulfonate group (SO$_3$R$^6$), a sulfate group (OSO$_3$R$^6$), a carboxyl group (CO$_2$H), a carbonyl group (COR$^E$), an ester group (CO$_2$R$^6$ or OCOR$^6$), an amide group (CONR$^6_2$ or NR$^6$COR$^6$), a carbamate group (NR$^6$CO$_2$R$^6$ or OCONR$^6_2$), a phosphate group (OPO$_3$R$^6_3$), a phosphonate group (PO$_3$R$^6_2$), an amino group (NR$^6_2$), an alkoxy group (OR$^6$), a thiol group (SR$^6$), a sulfoxy group (SOR$^E$), a sulfone group (SO$_2$R$^6$), a sulfonamide group (SO$_2$NR$^6_2$), a phosphino group (PR$^6_2$), a silane group (SiR$^6_3$), an optionally substituted straight-chain, branched or cyclic alkyl, alkenyl or alkynyl group wherein one or more C, CH or CH$_2$ groups can be replaced with O atom, N atom, S atom, NH group, CO group, OCO group, CONR$^6$ group, or an optionally substituted aromatic group. In these embodiments, each R$^6$ is independently hydrogen, an optionally substituted straight-chain, branched or cyclic alkyl, alkenyl or alkynyl group wherein one or more C, CH or CH$_2$ groups can be replaced with O atom, N atom, S atom, NH group, CO group, OCO group, CONR$^6$ group, or an optionally substituted aromatic group.

Two or more R$^5$ groups in these fluorophores can be linked together to form rings containing one or more of the same or different heteroatoms, such as O, N or S.

Substituents R$^5$ in these fluorophores that are not directly involved in attachment of self-immolative or urea-containing groups may be present in the molecule for other reasons. These reasons may include modification of spectroscopic characteristics of the dye, its solubility, chemical stability, charge, or photobleaching resistance. Some R$^5$ substituents may be useful for binding to a biomolecule or structure to be studied, such as nucleic acid, protein or lipid.

As discussed above, one of the R$^5$ or R$^6$ groups is, or can be substituted to contain, a reactive group thereby allowing the dyes of the present invention to be attached to an

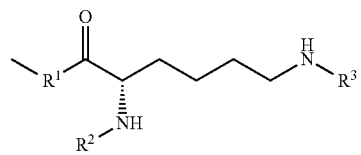

group. Examples of reactive groups that may find use in the present invention can include but not be limited to a nucleophilic reactive group, an electrophilic reactive group, a terminal alkene, a terminal alkyne, a platinum coordinate group or an alkylating agent.

There are a number of different electrophilic reactive groups that may find use in these embodiments. Examples include but not be limited to isocyanate, isothiocyanate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-proprionamide, glyoxal and aldehyde groups. Nucleophilic reactive groups can include but not be limited to reactive thiol, amine and hydroxyl groups. For purposes of synthesis of dyes, reactive thiol, amine or hydroxyl groups can be protected during various synthetic steps and the reactive groups generated after removal of the protective group.

One class of xanthene fluorophores useful in the present invention includes but not limited to rhodamine and rhodamine derivatives, such as Pennsylvania Green, Tokyo Green, Oregon Green, Singapore Green, and rosamines and rhodols and their derivatives. Some of these derivatives are shown below in Scheme II. The rhodamine, rosamine and rhodol backbone structures can be extended by adding additional rings as shown in Scheme III, or their appended phenyl ring might be missing to form aphenylic counterparts.

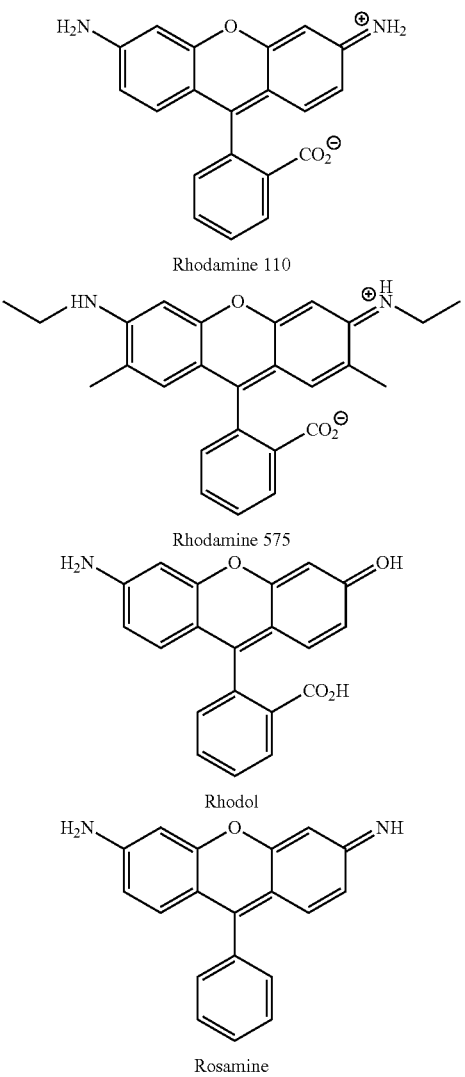

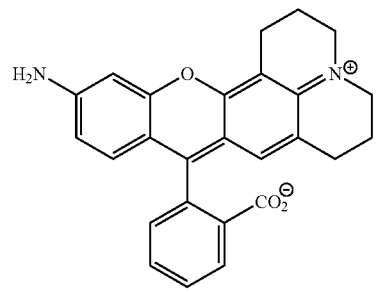

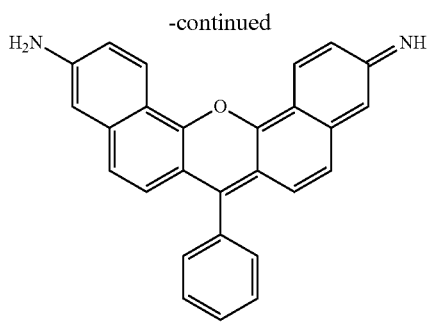

Another class of fluorescent dyes pertinent to the present invention is derivatized from the aforementioned rhodamines, rosamines and rhodols and can be represented by the general structures shown in Scheme IV.

Scheme IV

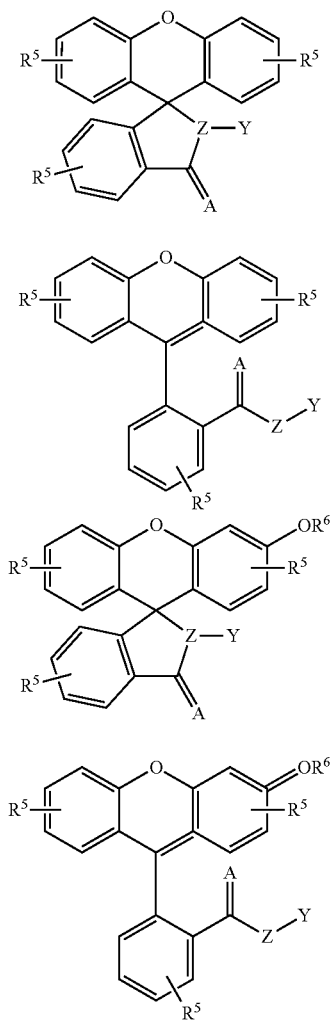

The substituent $R^5$ in Scheme IV is defined as described for Scheme I. The moiety A can be oxygen or sulfur while Z can be oxygen, sulfur or nitrogen unsubstituted or substituted with a group Y. The group Y, in turn, can be hydrogen, an optionally substituted straight-chain, branched or cyclic alkyl, alkenyl or alkynyl group wherein one or more C, CH or CH$_2$ groups can be replaced with O atom, N atom, S atom, NH group, CO group, OCO group, CONR$^3$ group, or an optionally substituted aromatic group. Y can also be another nitrogen, oxygen or sulfur atom substituted with hydrogen or an optionally substituted straight-chain, branched or cyclic alkyl, alkenyl or alkynyl group wherein one or more C, CH or CH$_2$ groups can be replaced with O atom, N atom, S atom, NH group, CO group, OCO group, CONR$^3$ group, or an optionally substituted aromatic group. The substituent Y can be a part of an aliphatic or aromatic cyclic structure such as morpholine, piperidine, pyrrolidine, piperazine, imidazole, triazole, oxazole, thiazole and others known in the art. Additionally, both Z and Y can contain electrophilic or nucleophilic reactive groups defined above.

Yet another class of fluorescent dyes pertinent to the present invention is based on coumarin and iminocoumarin backbone structure shown in Scheme V.

Scheme V

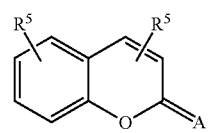

The substituent $R^5$ in the Scheme V represents functionalities defined in Scheme I above while A can be oxygen atom, O, or imino group, NH. Some of the compounds in this category are shown below in Scheme VI. The backbone structure can be extended by adding additional rings, aliphatic or aromatic, substituted or unsubstituted.

Scheme VI

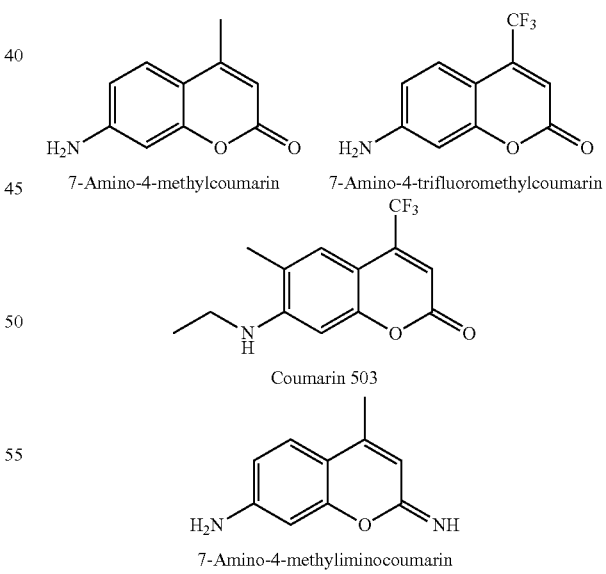

In other embodiments of the compounds of the present invention, SIG is a luminescent moiety. Any luminescent moiety, including any chemiluminescent or bioluminescent moieties, now known or later discovered, can be utilized in these embodiments. In some aspects of these embodiments, the compound comprises the structure:

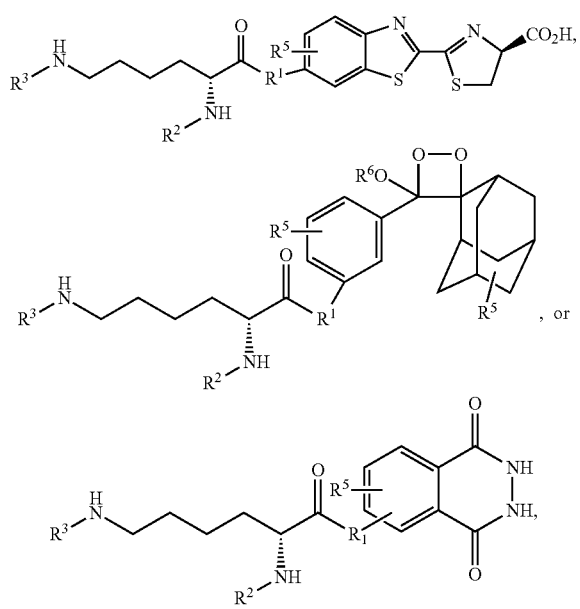

wherein each $R^5$ is independently hydrogen, a halogen (F, Cl, Br, I), a nitro group ($NO_2$), a nitroso group (NO), a hydroxylamino group (NHOH), a cyano group (CN), an isocyano group (NC), a thiocyano group (SCN), an isothiocyano group (SNC), an azido group ($N_3$), a trihalomethyl group ($CX_3$, where X is a halogen); a sulfonate group ($SO_3R^6$), a sulfate group ($OSO_3R^6$), a carboxyl group ($CO_2H$), a carbonyl group ($COR^E$), an ester group ($CO_2R^6$ or $OCOR^6$), an amide group ($CONR^6_2$ or $NR^6COR^6$), a carbamate group ($NR^6CO_2R^6$ or $OCONR^6_2$), a phosphate group ($OPO_3R^6_3$), a phosphonate group ($PO_3R^6_2$), an amino group ($NR^6_2$), an alkoxy group ($OR^6$), a thiol group (SR), a sulfoxy group ($SOR^6$), a sulfone group ($SO_2R^6$), a sulfonamide group ($SO_2NR^6_2$), a phosphino group ($PR^6_2$), a silane group ($SiR^6_3$), an optionally substituted straight-chain, branched or cyclic alkyl, alkenyl or alkynyl group wherein one or more C, CH or $CH_2$ groups can be replaced with O atom, N atom, S atom, NH group, CO group, OCO group, $CONR^6$ group, or an optionally substituted aromatic group; and each $R^6$ is independently hydrogen, an optionally substituted straight-chain, branched or cyclic alkyl, alkenyl or alkynyl group wherein one or more C, CH or $CH_2$ groups can be replaced with O atom, N atom, S atom, NH group, CO group, OCO group, $CONR^6$ group, or an optionally substituted aromatic group.

In some embodiments, the SIG is a fluorescent compound that targets a specific subcellular organelle, for example the lysosome, mitochondria, vacuole, nucleus or nucleolus. See, e.g., PCT/US10/002,494 and PCT/US10/02572 and references cited therein.

Specific examples of the invention compounds, as further described in the example below include

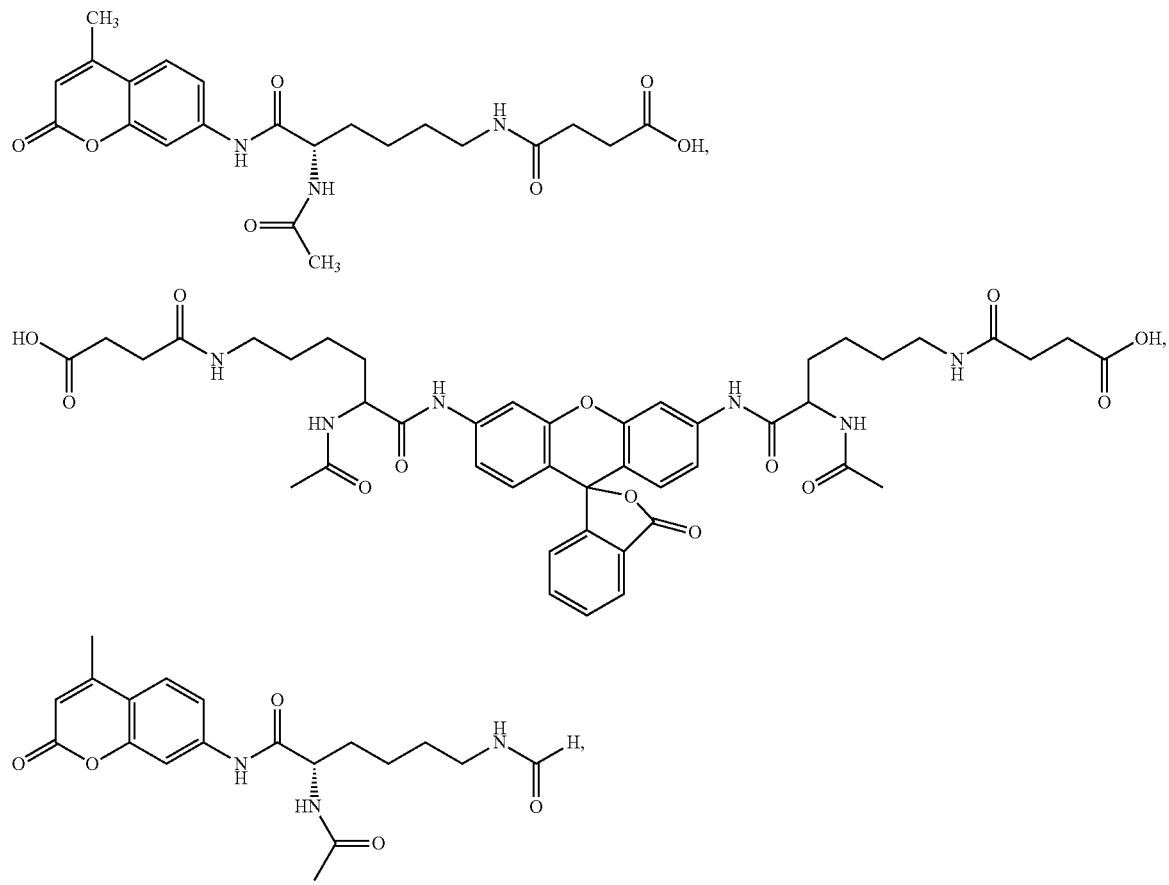

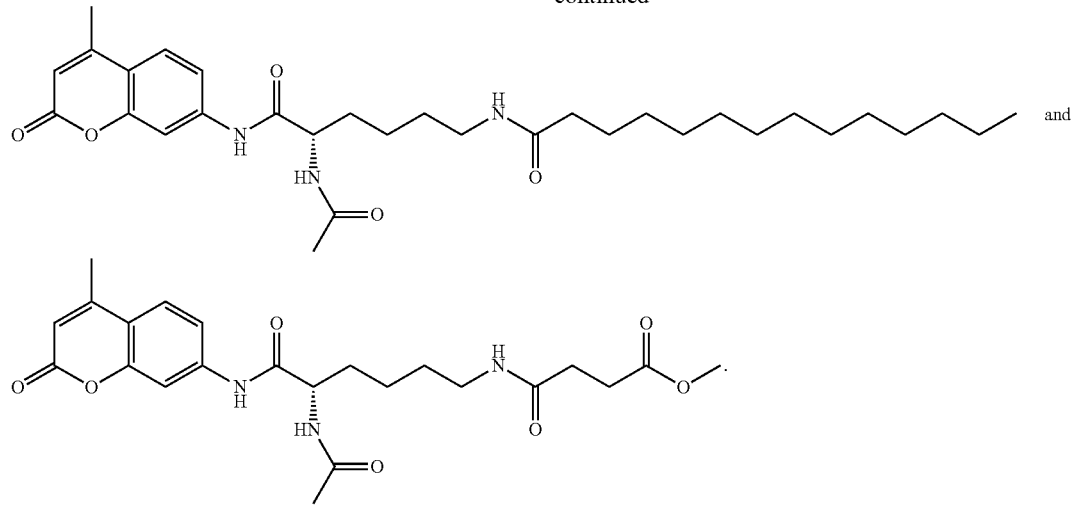

The first two compounds above are SIRT5 substrates, as they have a succinyl group as the $R^3$ moiety. See Example, where those two compounds are Compound 1 (Ac-Lys(Succ.)-AMC) and Compound 2 ((Ac-Lys(Succ.))$_2$-R110), respectively. Those compounds can be generalized as the formulas X-Lysine(ε-succinyl)-F and (X-Lysine(ε-succinyl))$_2$-F respectively, where, for both Compound 1 and Compound 2, X is an Nα acetyl function (Ac), and F is AMC, for Compound 1 and R110 (rhodamine green) for Compound 2. X could, however, be replaced by other N-terminal protecting groups, such as t-butyloxycarbonyl (Boc) or benzyloxycarbonyl (Cbz) or by peptide sequences of various lengths, while maintaining the essence of the assay principle (i.e. desuccinylation-dependent increase in a signal produced by a trypsin treatment, see FIG. 1). For example, the peptide substrate Ac-Arg-His-Lys-Lys(ε-acetyl)-AMC (Enzo Life Science Cat. #BML-KI177) is far more effective as a deacetylation substrate for SIRT5 than is Ac-Lys(Ac.)-AMC (Table 2; U.S. Patent Application Publication 20060014705). Thus, replacing X in either Compound 1 or Compound 2 with the sequence Ac-Arg-His-Lys could improve on these single-lysine SIRT5 desuccinylation substrates as the equivalent replacement improved on the single-lysine deacetylation substrate Ac-Lys(Ac.)-AMC. The sequence Arg-His-Lys-Lys is derived from residues 379-382 of p53 and a fraction of cellular p53 is localized to the mitochondria, including some in association with mitochondrial DNA in the matrix (Mahyar-Roemer et al., 2004; de Souza-Pinto et al., 2004; Chen et al., 2006; Bakhanashvili et al., 2008), the submitochondrial compartment containing most, if not all, SIRT5 (Michishita et al., 2005; Nakagawa et al., 2009). Thus it is possible that the affinity of SIRT5 for the p53 379-382 sequence reflects some in vivo association between the two proteins.

Other candidate amino acid sequences that might function well as the X group in SIRT5 substrates could be sought by means of an anti-succinyllysine antibody. The immunizing antigen for such an antibody may be prepared, for example, by succinylation of the protein keyhole limpet hemocyanin (KLH) with succinic anhydride, a procedure equivalent to that used to prepare the immunogens for rabbit polyclonal anti-propionyllysine and anti-butyryllysine antibodies (Enzo Life Sciences Cat. #s BML-SA683, BML-SA682). Production of the same immunogen via carbodiimide coupling and its use in preparation of a mouse monoclonal anti-succinyllysine have also been described (Kawai et al, 2006). An anti-succinyllysine antibody could be used to prepare an affinity chromatography matrix to enrich succinylated proteins from a mitochondrial or other cellular fraction. The succinylated proteins and the sequences surrounding their sites of lysine-succinylation could then be identified by established chromatographic and mass spectrometric procedures (Cheng et al., 2009). An anti-succinyllysine antibody could also form the basis of desuccinylation assays differing from the fluorometric assays already described (e.g. FIG. 1). SIRT5 or another desuccinylating enzyme would be brought into contact with lysine-succinylated peptides or proteins in the presence of appropriate cofactors (NAD$^+$ for SIRT5). The loss of lysine-succinylation would then be detected by standard immunochemical means (e.g. western blotting, ELISA).

Although one may yet be identified, there is currently no known N$^ε$-lysyl succinyltransferase that can perform protein lysyl succinylation using succinyl-CoA as the succinyl donor, a reaction analogous to those of the protein (histone) acetyltransferases (HATs); see Hodawadekar and Marmorstein, 2007. However, non-enzymatic succinylation of lysine by the peroxidation products of docosahexaenoic acid (DHA) has been demonstrated in vitro with peptides and proteins and the formation of protein succinyllysine residues in vivo has been shown to occur in DHA-fed mice subjected to oxidative stress (Kawai et al., 2006). Thus, another route to identification of the amino acid sequences proximal to native lysine succinylation sites would be to expose mitochondrial protein fractions to DHA oxidation products (Id.) and to then identify the sites by established chromatographic and mass spectrometric procedures (Cheng et al, 2009). Since these sites would be expected to include those that are targets of SIRT5 action in vivo, some of the sequences so identified would likely enhance the SIRT5 activity when incorporated into the "X" and/or "F" portions of synthetic substrate structures. Note that incorporation of a sequence from the N-terminal side of native SIRT1 deacetylation targets p53 Lys(Ac)-382 and histone H4 Lys(Ac)-16 has been shown to enhance activity relative to the single-lysine substrate Ac-Lys(Ac)-AMC and relative to substrates incorporating sequence from non-targeted sites (Howitz et al, 2003); Appendix E, Enzo Life Sciences Product instruction manual/assay kit protocol for SIRT1, Cat. #BML-AK555).

For Compound 1 and Compound 2, fitting the general formulas X-Lysine($\epsilon$-succinyl)-F and (X-Lysine($\epsilon$-succinyl))$_2$-F, signal generation is due to the bathochromic shift in fluorescence emission upon a desuccinylation-dependent trypsin-catalyzed release of the "F" function, where F is AMC, for Compound 1 and is either R110 (rhodamine green) or the mono-succinyllysine derivative (X-Lys (Succ.))-F for Compound 2. However, F could be any moiety that undergoes some spectroscopic change upon the desuccinylation-dependent hydrolysis of its bond with the carboxyl function of the lysine. For example, F could be p-nitroaniline (pNA), whose absorbance at 405 nm increases after trypsin hydrolysis of an amide bond between pNA and the lysine carboxyl (Appendix G, Enzo Life Sciences Instruction Manual for BML-AK501). Substrates with such dyes in the F position could be used in conjunction with one of the previously listed charge-neutralizing modifications to the distal carboxyl of the succinyl moiety, such as AM-esterification, thus combining an element that improves membrane permeability with one enabling targeting to SIRT5's subcellular location in the mitochondria or the nuclear location of class I HDACs.

For Compounds 1 and 2, and for those described immediately above, a dye group F in the structures X-Lysine($\epsilon$-succinyl)-F and (X-Lysine($\epsilon$-succinyl))$_2$-F directly forms a direct bond with the carbonyl of lysine and provides the assay signal upon desuccinylation-dependent trypsin cleavage of that bond. A substrate incorporating an equivalent desuccinylation-dependent signaling system could, alternatively, comprise the following: 1) a spectroscopically detectable function z that is part of either F or X, but does not form a direct covalent bond to the lysine carbonyl; and 2) a function q that is part of X if z is part of F or is part of F if z is part of X and which acts to suppress the detectable signal from z unless a desuccinylation-dependent cleavage of the bond between the lysine carbonyl and F occurs. An example of such a substrate is the peptide: (5-FAM)-QSTS<u>S</u><u>H</u><u>S</u>-K(Succ.)-LMFK(5(6)-TAMRA), (one-letter amino acid code, 5-FAM=5-carboxyfluorescein modifying the N-terminus, 5(6)-TAMRA=5-(and 6)-carboxytetramethylrhodamine modifying the $\epsilon$-amino of the lysine side chain). This peptide comprises the residues 375-386 of p53, but is modified by R(379)S and K(381)S substitutions to eliminate trypsin-cleavable sites (underlined) and is succinylated on the $\epsilon$-amino of K(382). In terms of the generalized structure, X-Lysine($\epsilon$-succinyl)-F, (5-FAM)-QSTS<u>S</u><u>H</u><u>S</u> is X, LMFK(5(6)-TAMRA) is F, z is 5-FAM and q is 5(6)-TAMRA. In the intact peptide, the fluorescence of the 5-FAM (Ex. 492 nm; Em. 518 nm) is quenched by resonance energy transfer due to proximity and spectral overlap with 5(6)-TAMRA (Ex. 542 nm; Em. 568). Desuccinylation-dependent trypsin cleavage after K(382) would produce a fluorescein fluorescence signal by separating the 5-FAM from the quenching 5(6)-TAMRA. Replacement of trypsin with the similar, but lysine-specific, enzyme lysyl endopeptidase (EndoLysC; EC 3.4.21.50) would allow the inclusion of arginine residues (trypsin cleavable sites) in sequence intervening between the signaling "z" function and the signal-suppressing "q" function. In the preceding example, the q group suppresses the signal from the z group by fluorescence resonance energy transfer, but with different types of q moieties other mechanisms may be employed. For example, q could be an affinity tag such as biotin, allowing the physical removal of the background fluorescence inherent in the remaining succinylated/uncleaved peptide by means of the biotin-binding protein streptavidin linked to a solid support such as agarose beads.

Figure 7:
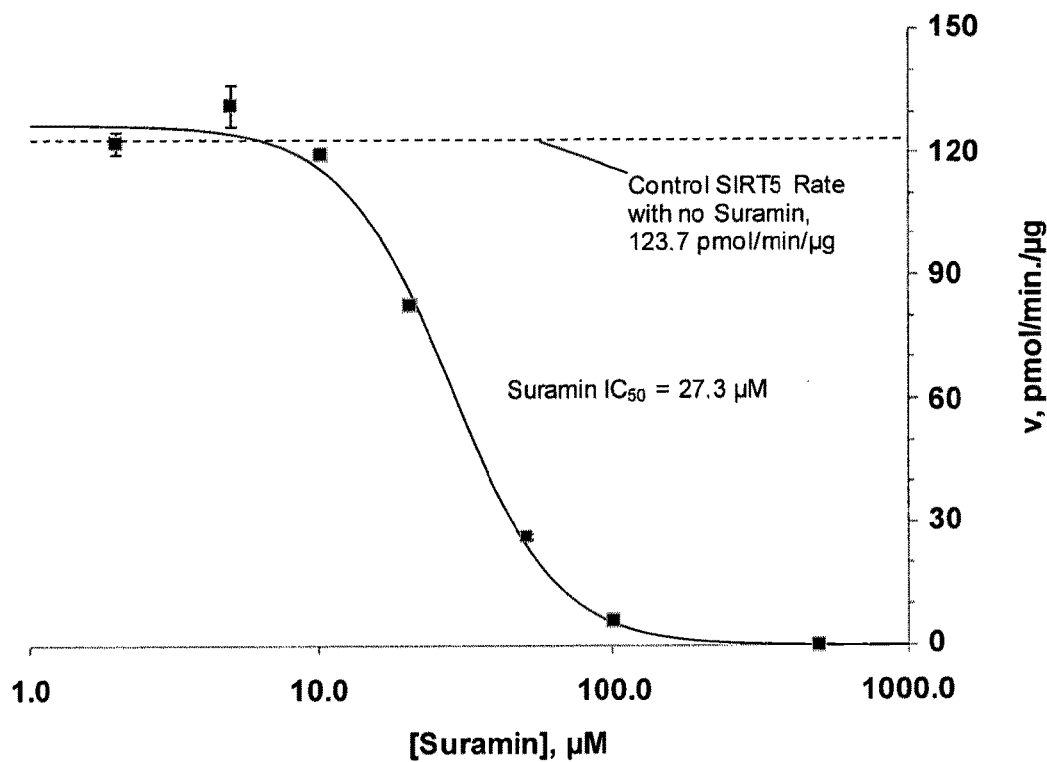
FIG. 7 is a graph showing the inhibition of SIRT5 desuccinylation of Ac-Lys(Succ.)-AMC by suramin. Desuccinylation reaction conditions were as described (FIG. 5), but done for 60 min. at 37° C., with the indicated concentrations of suramin (ENZO Life Sciences Cat. #ALX-430-022) and with constant concentrations of 50 μM Ac-Lys(Succ.)-AMC, 500 μM NAD and 12 nM SIRT5 (20 ng/50 μl). Signal development (trypsin treatment) and fluorescence readings were done as described, as were the conversion of fluorescence increases to rates in units of pmol/min/μg (FIG. 5). Data points represent the mean of three determinations and the error bars are the standard deviations from those means. The dose-response curve was derived from a least-squares fit to a three parameter Hill-Slope model (bottom fixed at 0 pmol/min/μg.), $y=top/(1+(x/IC_{50})^{slope})$. The fitted parameters were top=127 pmol/min/μg, $IC_{50}$=27.3 μM and slope=2.37 ('Solver' tool, Microsoft XL).
Figure 8:
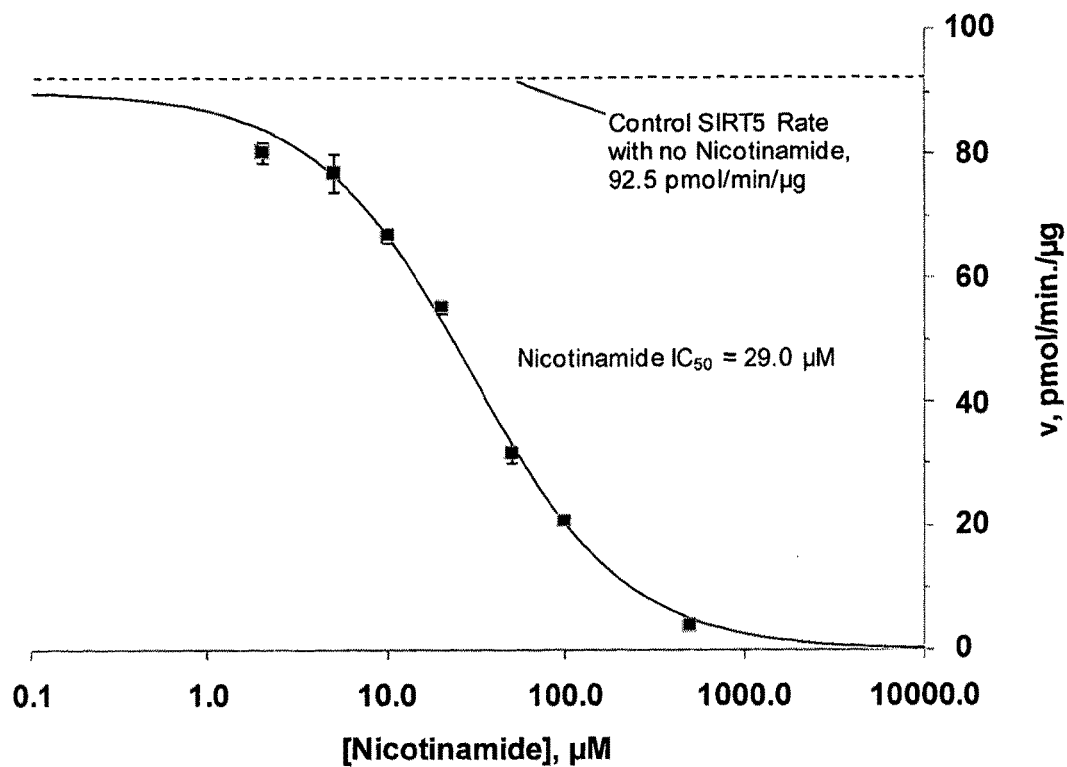
FIG. 8 is a graph showing inhibition of SIRT5 desuccinylation of Ac-Lys(Succ.)-AMC by nicotinamide. All reaction conditions and procedures were as described for the suramin inhibition study (FIG. 7) but reactions were done instead with the indicated concentrations of nicotinamide (ENZO Life Sciences Cat. #BML-KI283). Data points represent the mean of three determinations and the error bars are the standard deviations from those means. The dose-response curve was derived from a least-squares fit to a three parameter Hill-Slope model (bottom fixed at 0 pmol/min/μg.), $y=top/(1+(x/IC_{50})^{slope})$. The fitted parameters were top=90.2 pmol/min/μg, $IC_{50}$=29.0 μM and slope=0.98 ('Solver' tool, Microsoft XL).
Figure 9:
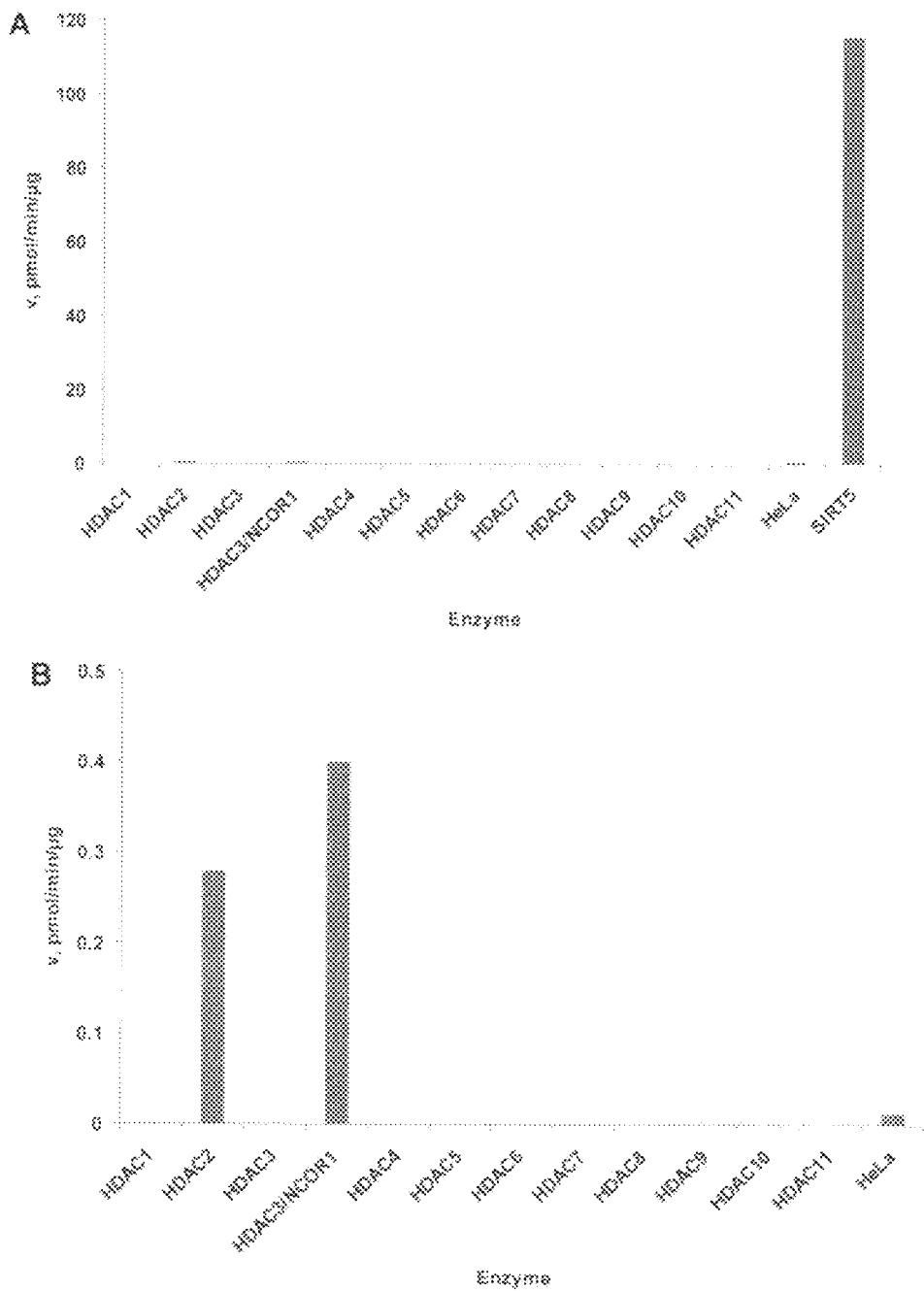
FIG. 9 is graphs showing the high specific activity of SIRT5 catalyzed NAD$^+$-dependent desuccinylation of Ac-Lys(ε-succinyl)-AMC compared with minor activities of non-SIRT HDACs and HeLa nuclear extract. Initial rate activities of the indicated enzyme were determined with 50 μM Ac-Lys(Succ.)-AMC for HDACs 1-11 and HeLa nuclear extract. SIRT5 activity was determined with 50 μM Ac-Lys (Succ.)-AMC plus 500 μM NAD⁺. Panels A and B present the same data, but with the SIRT5 bar omitted from B in order to display the remaining bars at a 240-fold higher scale.
Figure 10:
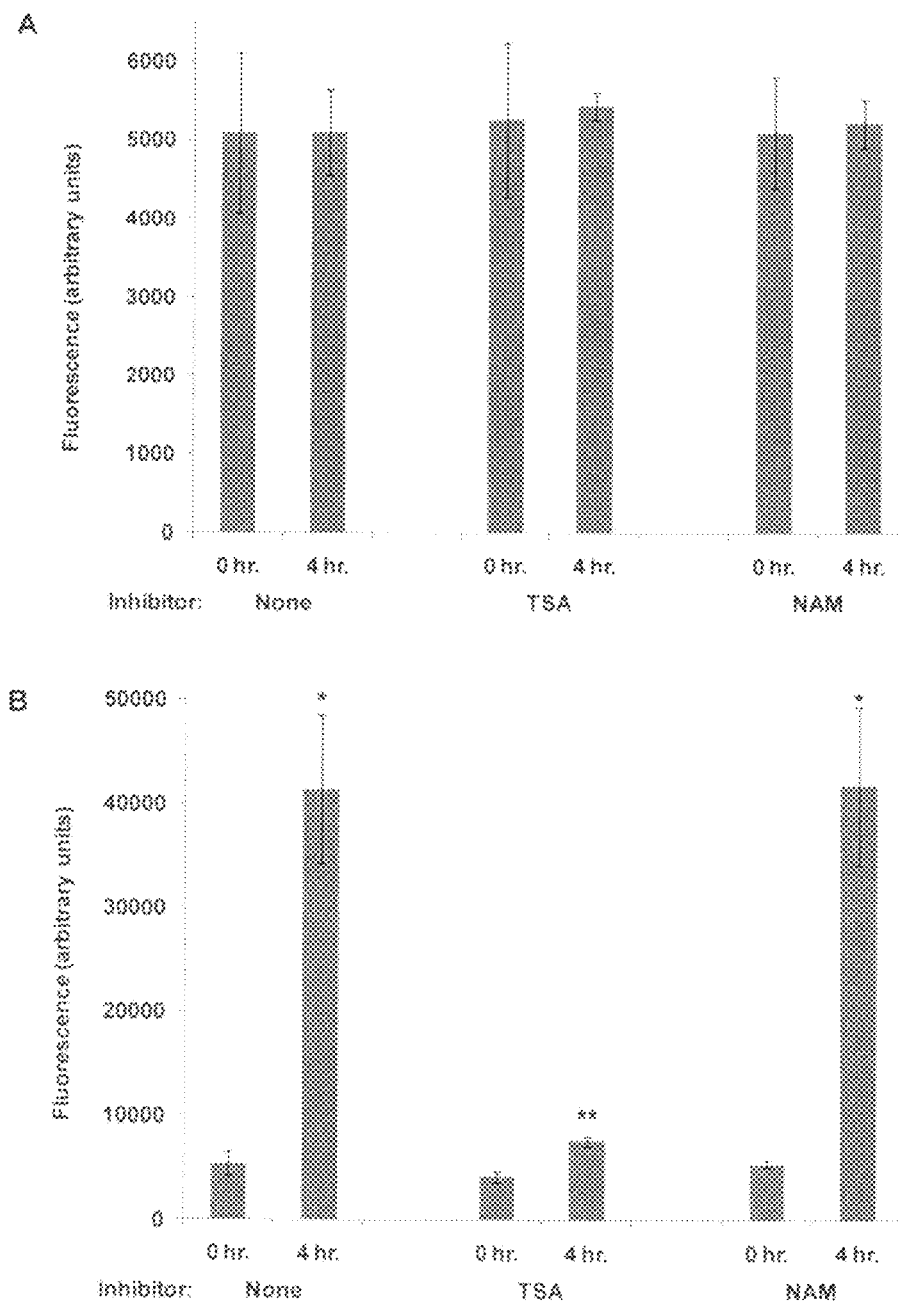
FIG. 10 is graphs showing that intact HeLa cells do not significantly desuccinylate Ac-Lys(ε-succinyl)-AMC under the conditions that allow deacetylation of Ac-Lys(ε-acetyl)-AMC. HeLa cells were cultured to 95% confluence in the wells of ½-volume 96-well plates. Either 200 μM Ac-Lys (Succ.)-AMC (Panel A) or 200 μM Ac-Lys(Ac.)-AMC (Panel B) was added to the medium, either alone or with trichostatin A (TSA, 1 μM) or nicotinamide (NAM, 1 mM). After the indicated time, cells were lysed with detergent and trypsin added to release AMC from desuccinylated or deacetylated substrate and then fluorescence read (Ex. 360 nm/Em. 460 nm). For "0 hr." samples, substrate, inhibitors, lysis buffer and trypsin were added simultaneously. Bars represent the mean of three determinations and the error bars the Standard Deviation from that mean. Statistically significant differences between the fluorescences of "4 hr." and "0 hr." samples (Student's t-test) are indicated by asterisks as follows: *, p<0.02; **, p<0.002.
Figure 11:
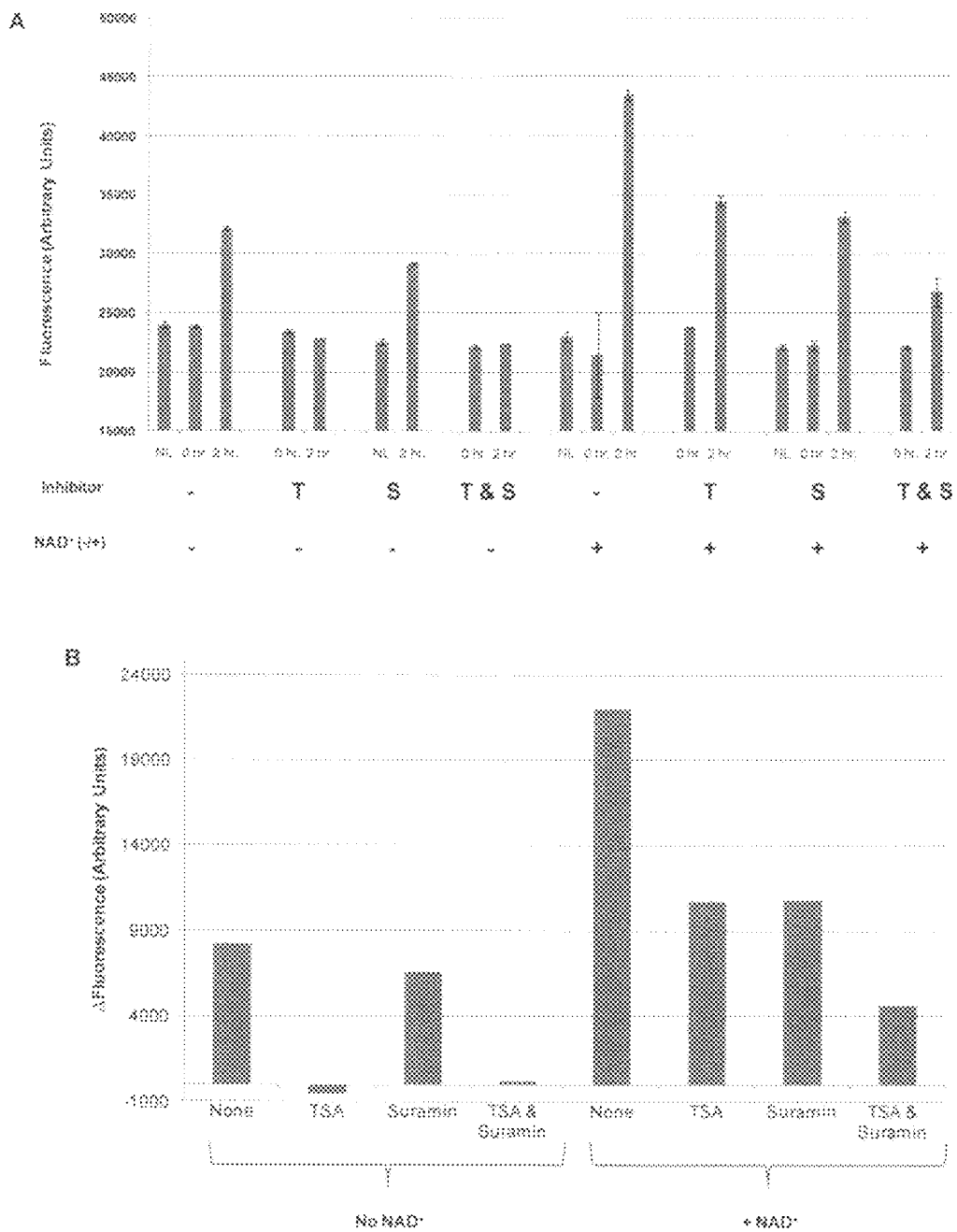
FIG. 11 is graphs showing that HeLa cell extracts have Ac-Lys(ε-succinyl)-AMC desuccinylation activity that is partially NAD⁺-dependent/suramin-sensitive (SIRT5) and partially TSA-sensitive (class I HDACs). HeLa cell extracts were prepared by hypotonic/detergent lysis (0.5% NP-40) and assayed for Ac-Lys(ε-succinyl)-AMC desuccinylation activity (extract equivalent to 28×10⁴ cells per assay well). Panel A shows cell extracts incubated with 50 μM Ac-Lys (Succ.))-AMC and incubated for 0 hr. or 2 hr. (37° C.) with indicated additions. "No Lysate" (NL) sample contained only the buffer of equivalent to that of the cell extracts and these samples were incubate 2 hr. T=TSA (1 μM) and S=suramin (200 μM). NAD⁺, when present, was 500 μM. At the end of the substrate incubations, AMC was cleaved from desuccinylated substrate by trypsin treatment and fluorescence determined (Ex. 360 nm, Em. 460 nm). Bars represent the mean of two determinations and the error bars the standard deviations from those means. Panel B shows the fluorescence increases from 2 hr. of extract activity were calculated by subtracting the corresponding 0 hr. data from the 2 hr. data in Panel A. For the No NAD⁺/Suramin data there were no 0 hr. samples and the corresponding NL value was subtracted instead. Bars are labeled to indicate which inhibitor(s), if any, were present.

The succinylated substrate Ac-Lys(Succ.)-AMC (Compound 1), in addition to providing a highly effective and convenient means of SIRT5 assay, also provided the means to discover a surprisingly strong, TSA-sensitive desuccinylase activity in HeLa cell extracts, in all likelihood due to class I HDACs (see FIG. 11, Table 2 and FIG. 9). This substrate could also be used in the processes of: 1) purifying and identifying the particular TSA-sensitive enzyme or enzymes that contribute to this desuccinylase activity, 2) locating the subcellular compartment in which the activity resides, 3) isolating any multiprotein complexes harboring desuccinylase activity and 4) determining which protein binding partners enhance the catalytic activity of the TSA-sensitive desuccinylase(s). As will be discussed below, there are reasons to suspect that the $\epsilon$-amino function of the lysine side-chain of proteins in vivo may be subject to a wide variety of novel, non-acetyl acylations in addition to succinylation. By replacing the succinyl moiety in Compound 1 or Compound 2 or in any of the structural variants of X-Lysine($\epsilon$-succinyl)-F or (X-Lysine($\epsilon$-succinyl))$_2$-F described above, a tool for discovery of deacylase enzymes and the mechanisms that regulate their activities (processes 1-4, above) could be constructed for each type of $N^\epsilon$-acyllysine modification. Once a new deacylase was identified, the corresponding lysine-acylated substrate or substrates could be used for the same types of compound screening for drug discovery, kinetic characterization, mechanistic studies and further assay development as described for the succinyl substrate 1 (FIGS. 4-8, 10, 11).

One reason for the prediction that additional non-deacetylase/non-desuccinylase lysyl deacylase activities remain to be discovered is the documented existence of in vivo modifications to the $\epsilon$-amino group of lysine that derive from reaction with oxidative breakdown products of various biomolecules. For example, 3'-formylphosphate, which arises from the 5'-oxidation of deoxyribose in DNA leads to the $N^\epsilon$-formylation of lysines in histones and this process is stimulated by oxidative stress (Jiang et al., 2007). Formylation of the linker histone H1 is especially prevalent (Wisniewski et al., 2007), but also extends to the N-terminal tails and globular domains of core histones and other nuclear proteins (Wisniewski et al., 2008). Such modifications would be expected to interfere with chromatin structure (DNA binding by histone H1 and core histones) and with the system of epigenetic lysine modifications (acetylation, methylation especially in core histone N-terminal tails) that function in the regulation of gene expression. Therefore a lysine deformylase that functions as a repair enzyme in response to oxidative stress damage must be considered a distinct possibility and substrates of type X-Lysine($\epsilon$-formyl)-F or (X-Lysine($\epsilon$-formyl))$_2$-F would be useful for the same processes described above for succinylated substrates.

Peroxides derived from the oxidation of polyunsaturated fatty acids (PUFAs) can react with cellular proteins to form novel $N^\epsilon$-acylated lysine residues (for review see Kato and Osawa, 2010). As noted above, protein lysine residues can be succinylated by reaction with the peroxidation products of DHA, a PUFA (Kawai et al., 2006). In addition, PUFA-derived N$_\epsilon$-acyl-lysine adducts can include the hexanoyl, glutaroyl and azelayl acylations. Similar to the formyl modification, these are the result of oxidative stress and could be disruptive to protein function. Therefore, lysine deacylases specific for these modifications and that function as repair enzymes in response to oxidative stress damage must be considered a distinct possibility. Thus substrates of type X-Lysine($\epsilon$-acyl)-F or (X-Lysine($\epsilon$-acyl))$_2$-F would be useful for the same discovery processes described above for succinylated substrates. The $\epsilon$-acyl functions would include the hexanoyl, glutaroyl and azelayl moieties.

As noted earlier, N$^\epsilon$-acetylation of protein lysine residues is catalyzed by transferases that use acetyl-CoA as the donor of the acetyl group. There are twenty-six acyl-coenzyme A synthetases in the human genome (Watkins et al., 2007) and the Human Metabolome Database lists 134 acyl-CoAs that could be the source of novel lysine acylations catalyzed by hitherto unidentified transferase enzymes (see the website hmdb.ca/search/search?query=%22CoA%22), exclusive of: 1) CoA itself, 2) acetyl-CoA, propanoyl-CoA, butyryl-CoA (known substrates of the acetyltransferases (HATs)), 3) propinol, propinol adenylate, 3-hydroxyvaleric acid (non-CoA metabolites). Each of these may be considered a potential acyl donor for transfer to the N$^\epsilon$-amino function of protein lysines and consequently substrates of type X-Lysine ($\epsilon$-acyl)-F or (X-Lysine($\epsilon$-acyl))$_2$-F, where the $\epsilon$-acyl function is any of the 134 cited above, would be useful for the same types of discovery processes described above for succinylated substrates. For one of these acyl-CoA's, myristoyl-CoA, there is evidence for its use in transfer to specific lysine residues in the precursor protein of tumor necrosis factor α (Stevenson et al., 1992) and in the precursor protein of interleukin 1α (IL-1α) (Stevenson et al., 1993).

Any of the above-described compounds can be packaged in a kit for commercial sale. In some embodiments, the kit further comprises instructions for determining the presence of the enzyme, or instructions for determining the presence of an inhibitor of the enzyme. In some of these embodiments, the enzyme is a histone deacetylase (HDAC), for example, a sirtuin, e.g., SIRT5. An example of a compound that could usefully be packed in a kit is

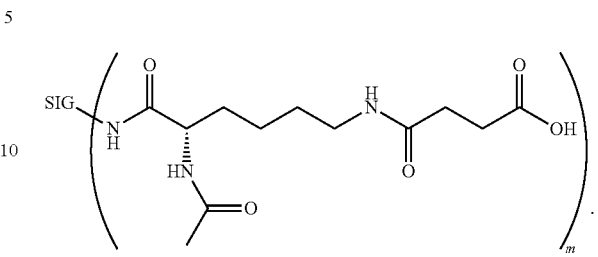

More specific examples include

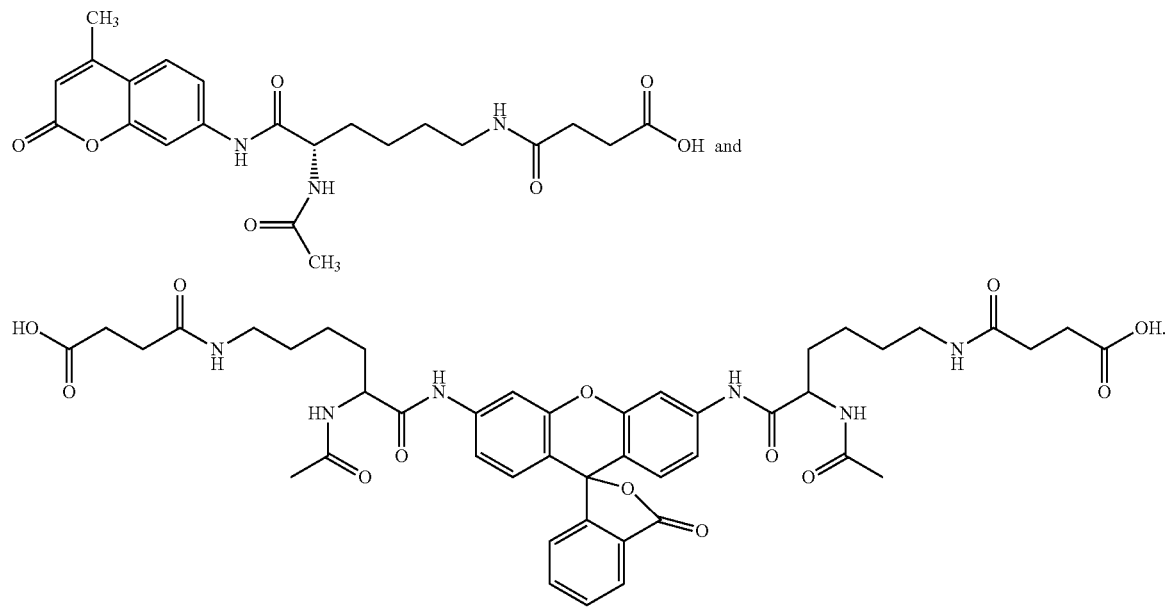

These kits can also contain other reagents that are useful for determining the presence of the enzyme or an inhibitor of the enzyme. Non-limiting examples of such reagents include a standard of a known concentration of the enzyme and/or an inhibitor of the enzyme, a peptidase (e.g., trypsin), luciferase if SIG is a luciferase substrate, and/or appropriate buffers.

The present invention is also directed to a method of determining whether a sample has an enzyme that removes a moiety from an $\epsilon$-amino of a lysine, where the moiety is a succinyl, a methyl succinyl, a formyl, or a myristoyl. The method comprises (a) combining the sample with any of the above-described compounds to make a sample-compound mixture, where R$^3$ of the compound is the moiety;

(b) incubating the sample-compound mixture under conditions and for a time sufficient to allow the enzyme to remove the R$^3$; and (c) determining whether the R$^3$ is removed from the compound. In these methods, removal of R$^3$ from the compound indicates that the sample has the enzyme.

The proper conditions for incubating the sample-compound mixture could be determined for any particular enzyme without undue experimentation. For example, when the enzyme is a class III HDAC [sirtuin]), NAD+ should be present.

The determination of whether the $R^3$ moiety is removed can be by any means known in the art, for example by mass spectroscopy, an immunoassay with an antibody that can distinguish between the compound with the $R^3$ group and without it, or an appropriate chromatographic method. In some embodiments, the compound is a substrate for a peptidase after the enzyme cleaves $R^3$ from the compound but not if the $R^3$ is not removed from the compound. In such as case, the determining step further comprises
(i) adding the peptidase to the mixture for a time sufficient for the peptidase to cleave the resulting molecule between the $R^1$ and the CO moieties, such that SIG generates an increased signal relative to the signal generated with the compound; and
(ii) determining whether SIG generates an increased signal relative to the signal generated with the compound. Here, an increased signal (e.g., greater fluorescence) indicates that the sample has the enzyme.

The present methods are not narrowly limited to the use of any particular peptidase. In various embodiments, the peptidase is a trypsin (e.g., where the $R^3$ group is a succinyl, a methyl succinyl, or a myristoyl group) or an endoproteinase Lys-C.

These methods can be utilized with a sample from any source. In some embodiments, the sample is a purified preparation of the enzyme. In other embodiments, the sample is an extract of a cell, tissue or organ of a multicellular eukaryote, for example a mammal. The sample can comprise, for example, a living cell or a homogenized mixture from tissue.

These methods are not limited to detection of any class of enzyme, provided the enzyme is capable of removing the $R^3$ moiety from the compound. In some embodiments, the enzyme is a histone deacetylase (HDAC), for example a sirtuin, e.g., SIRT5.

An example of a compound useful for these methods is

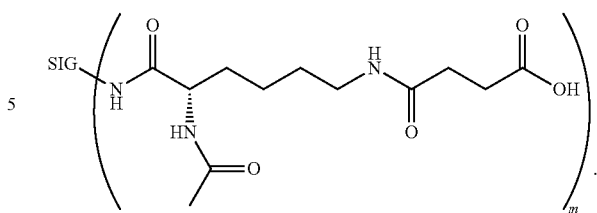

More specific examples include

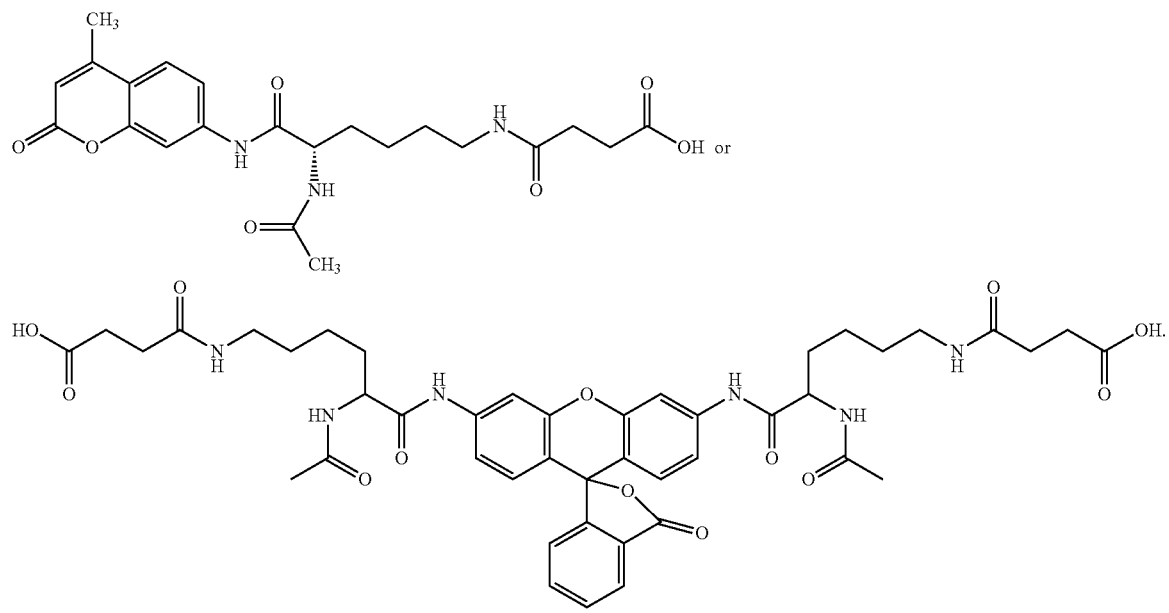

In some embodiments of these methods, the enzyme is quantified in the sample by measuring the rate of removal of the $R^3$ moiety and comparing that rate to the rate of removal of a known amount of the enzyme (i.e., comparing to a standard curve of the enzyme action on the compound). In various embodiments, the rate of removal is determined by the increased signal from SIG after addition of a peptidase, and comparing the increased signal to a standard curve that provides the quantity of the enzyme that leads to the increased signal.

The above-described compounds can also be used to identify an inhibitor for an enzyme that removes the $R^3$ moiety from any of the above-described compounds, by determining whether a putative inhibitor prevents removal of the $R^3$ moiety from the compound. Thus, the invention also is directed to a method of determining whether a molecule inhibits an enzyme that removes a moiety from an s-amino of a lysine, where the moiety is a succinyl, a methyl succinyl, a formyl, or a myristoyl. The method comprises
(a) combining the enzyme and the molecule with any of the above-described compounds to make an enzyme-molecule-compound mixture, where $R^3$ of the compound is the moiety;

(b) incubating the enzyme-molecule-compound mixture under conditions and for a time sufficient for the enzyme to remove the moiety in the absence of the molecule; and (c) determining whether the $R^3$ is removed from the compound to an equivalent degree that $R^3$ would be removed from the compound in the absence of the molecule. In these methods, the failure of the removal of $R^3$ from the compound to an equivalent degree as in the absence of the molecule indicates that the molecule is an inhibitor of the enzyme.

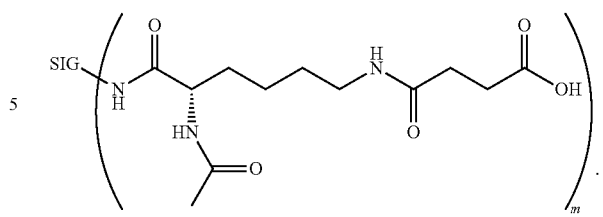

More specific examples include

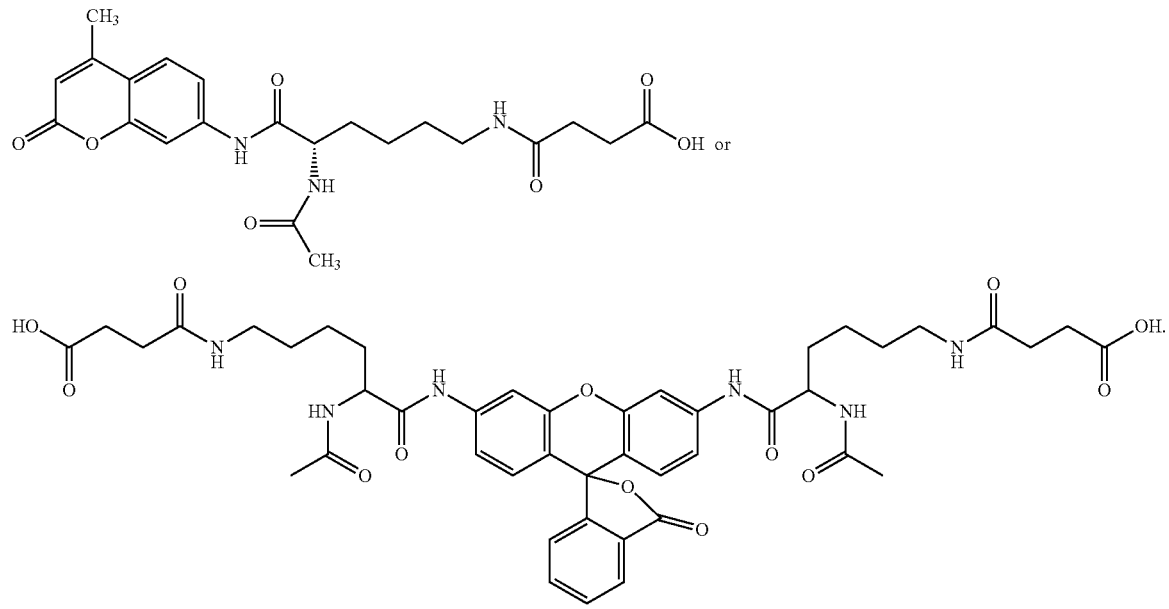

The determination of whether the $R^3$ moiety is removed can be by any means known in the art, for example by mass spectroscopy, an immunoassay with an antibody that can distinguish between the compound with the $R^3$ group and without it, or an appropriate chromatographic method. In some embodiments, the compound is a substrate for a peptidase after the enzyme cleaves $R^3$ from the compound but not if the $R^3$ is not removed from the compound. In such as case, the determining step further comprises (i) adding the peptidase to the mixture for a time sufficient for the peptidase to cleave the resulting molecule between the $R^1$ and the CO moieties, such that SIG generates an increased signal relative to the signal generated with the compound; and (ii) determining whether SIG generates an increased signal relative to the signal generated with the compound. Here, an increased signal indicates the removal of $R^3$ from the compound.

These methods are not narrowly limited to the use of any particular peptidase. In various embodiments, the peptidase is a trypsin (e.g., where the $R^3$ group is a succinyl, a methyl succinyl, or a myristoyl group) or an endoproteinase Lys-C.

Further, these methods are not limited to detection of any class of enzyme, provided the enzyme is capable of removing the $R^3$ moiety from the compound. In some embodiments, the enzyme is a histone deacetylase (HDAC), for example a sirtuin, e.g., SIRT5.

An example of a compound useful for these methods is

These methods can utilize high-throughput and automation methods and equipment known in the art to assay more than one molecule simultaneously. Such methods are useful for assaying any number of compounds, for example from a chemical library. In some embodiments, more than 10 molecules are subjected to the method simultaneously. In other embodiments, more than 50 molecules are subjected to the method simultaneously.

Preferred embodiments are described in the following example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example. Compounds and Methods for Detecting SIRT5

The compound, N—($N^\alpha$-acetyl-L-Lysine($N^\epsilon$-succinyl))-AMC (Ac-Lys(Succ.)-AMC; AMC=7-amino-4-methylcoumarin) is depicted as Compound 1 and was synthesized as follows. Succinic anhydride (0.2 mmol, 0.020 g) was added under an argon atmosphere to a suspension of Ac-Lys-AMC (0.2 mmol, 0.069 g) in DMF (1.3 ml). The mixture was stirred for four hours at room temperature. All volatility was evaporated under vacuum. The residue was purified by flash chromatography (silica gel; 5% to 15% MeOH in $CH_2Cl_2$) to give a yellowish solid as an impure compound. The mixture was further purified by reverse phase chromatography (C18 silica gel, 100% $H_2O$ to 15% $H_2O$ in MeOH to 100% MeOH) to afford 0.077 g of Ac-Lys(Succ.)-AMC as an off-white pure solid (purity >98% TLC, $R_f$: 0.45, 20% MeOH/CH$_2$Cl$_2$, 86% yield); C$_{22}$H$_{27}$N$_3$O$_7$, FW: 445.50.

The $^1$H-NMR spectrum and mass spectroscopy analysis (MS:468.1 (M+Na$^+$)) were consistent with the structure depicted as Compound 1, Ac-Lys(Succ.)-AMC.

1

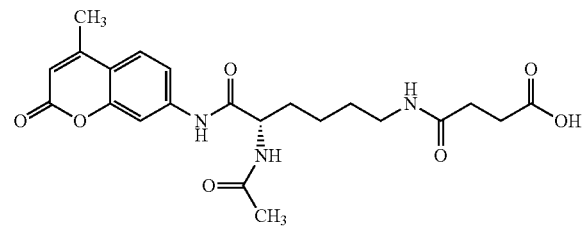

The compound, N,N'-Bis(α-acetyl-Lysine(ε-succinyl))-rhodamine 110 ((Ac-K(Succ.)$_2$-R110) was prepared as follows. Pyridine (1 ml) and 1-ethyl-(3-dimethylaminopropyl)-carbodiimide hydrochloride (1.4 mmol, 0.268 g, Chem-Impex-International, Cat. #00050) was added to a solution of Rhodamine Green 560 chloride (rhodamine 110, 0.5 mmol, 0.183 g) and Ac-Lys(Boc)-OH (1.05 mmol, 0.303 g, Bachem Cat. #E1040) in DMF (1 ml) at 0° C. under an argon atmosphere. The mixture was stirred at room temperature overnight. All volatility was evaporated by vacuum. The residue was purified by flash chromatography (silica gel; 5% to 15% MeOH in CH$_2$Cl$_2$) to yield a yellowish, semisolid impure intermediate (0.24 g, 28% yield). The intermediate (0.24 g, 0.27 mmol) was dissolved in CH$_2$Cl$_2$ (1.5 ml). Trifluoroacetic acid (1.5 ml) was added to this solution at 0° C. The mixture was stirred at room temperature for 1 hour. All the solvents were evaporated by rotary evaporator to give 0.20 g of the deprotected (deBOC) compound. Succinic anhydride (0.075 g, 0.075 mmol) was added to a suspension of the deBOC compound (0.10 g, 0.15 mmol) in DMF (1 ml). The resulting mixture was stirred overnight under an argon atmosphere at room temperature. All volatility was evaporated and the mixture was purified by flash chromatography (10% to 30% MeOH in CH$_2$Cl$_2$) to yield a yellow, solid mixture. The mixture was purified again by reverse phase chromatography (C18 silica gel, 100% H$_2$O to 10% H$_2$O in MeOH to 100% MeOH) to afford 0.022 g of pure compound: C$_{44}$H$_{50}$N$_6$O$_{13}$, FW: 870.90. The NMR spectrum was consistent with the structure depicted as Compound 2, N,N'-Bis(α-acetyl-Lysine(ε-succinyl))-rhodamine 110 ((Ac-K(Succ.))$_2$-R110).

The compound N—(N$^\alpha$-acetyl-L-Lysine(N$^\epsilon$-formyl)) AMC (Ac-Lys(Form.)-AMC) is depicted as Compound 3 and was synthesized as follows: Acetic anhydride (0.06 ml, Aldrich) was added to a suspension of Ac-Lys-AMC (0.0143 g, 0.041 mmol, Bachem 1-1040) in dry formic acid (0.15 ml, treated by 3 Å molecular sieves) slowly with stirring over a period of 7 minutes under an argon atmosphere at 0° C. The mixture was stirred for two hours at room temperature and was then quenched into ether (50 ml). A precipitate was formed and the precipitate was further washed by ether. After filtering off the solution, the mixture was purified by reverse phase chromatography (C18 silica gel, 100% H$_2$O to 100% MeOH) to afford 0.010 g of impure compound as an off-white solid. The solid was crystallized from MeOH to afford 0.0085 g of Ac-Lys-N$^\epsilon$-Formyl-AMC as a white solid (R$_f$: 0.10, 50% MeOH/CH$_2$Cl$_2$, 55% yield), C$_{19}$H$_{23}$N$_3$O$_5$, FW: 373.40. The NMR spectrum was consistent with the structure depicted as Compound 3.

3

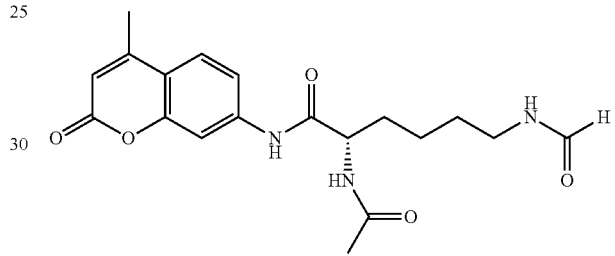

The compound, N—(N$^\alpha$-acetyl-L-Lysine(N$^\epsilon$-myristoyl))-AMC, Ac-Lys(Myr.)-AMC is depicted as Compound 4 and was prepared as follows. Myristoyl chloride (0.024 g, 0.010 mmol) was added to a suspension of Ac-Lys-AMC (0.022 g, 0.065 mmol) in DMF (1.0 ml) and pyridine (0.2 ml) slowly with stirring over a period of 5 minutes under argon atmosphere at 0° C. The mixture was stirred overnight at room temperature. After all volatility was evaporated under vacuum, the residue was purified by flash chromatography (silica gel, from 1% methanol in methylene chloride up to 20% methylene chloride) to afford 0.016 g of pure compound as a white solid. (R$_f$: 0.48, 10% MeOH/CH$_2$Cl$_2$, 55% yield), C$_{44}$H$_{50}$N$_6$O$_{13}$, FW:555.75. The NMR spectrum was consistent with the structure depicted as Compound 4.

2

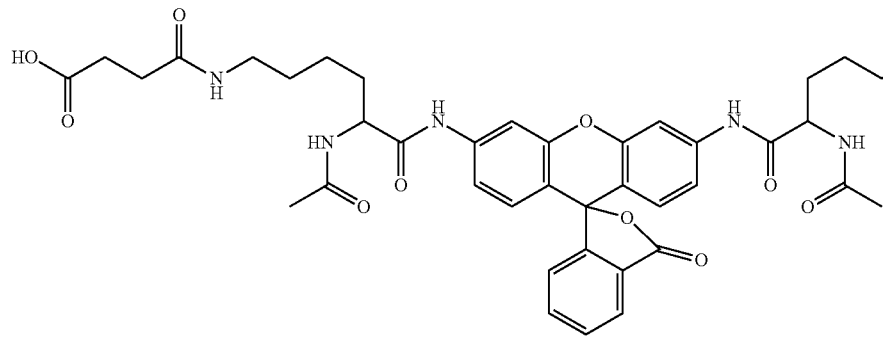

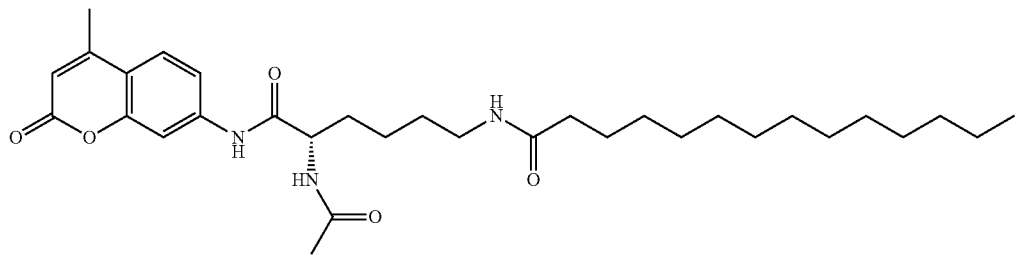

4

The compound, N—(N$^\alpha$-acetyl-L-Lysine(N$^\epsilon$-methyl succinyl))-AMC (Ac-Lys(Methyl Succ.)-AMC) is depicted as Compound 5 and was prepared as follows. To a suspension of Ac-AMC-Succinyl-Lys (0.018 g, 0.040 mmol) in ether (0.3 ml) was added freshly made diazomethane (2 ml) under an argon atmosphere at 0° C. The mixture was stirred for two hours at room temperature. All volatility was evaporated and diazomethane (2 ml) was added again. The mixture was stirred another one hour at room temperature. After all volatility was evaporated, the residue was purified by flash chromatography (MeOH in methylene chloride from 5% to 20%) to give Ac-Lys(Methyl Succ.)-AMC (0.015 g, 82% yield) as a white solid ($R_f$: 0.31, 20% MeOH/CH$_2$Cl$_2$), C$_{23}$H$_{29}$N$_3$O$_7$, FW:459.49. The NMR spectrum was consistent with the structure depicted as Compound 5.

5

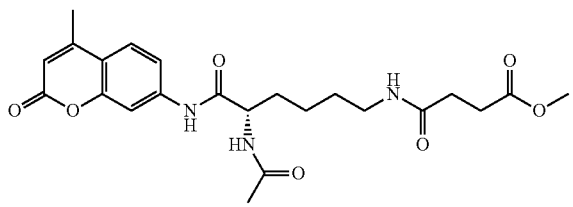

As noted in the Background of the Invention section above, the protease trypsin catalyzes the hydrolytic cleavage of amide bonds on the carboxyl side of unmodified lysine residues. Hydrolytic cleavage of lysyl amide bonds with AMC or rhodamine 110 (dye components of Compounds 1 and 2, respectively) releases the free amino forms of the dyes. This elicits an upward shift of the dye's fluorescence emission peak wavelength (bathochromic shift), for example to 460 nm for AMC or 530 nm for rhodamine 110. If succinylation of the $\epsilon$-amino function of the lysine moieties in compounds such as 1 and 2 renders the amide bond between the carbonyl of lysine and the amino of dye groups such as AMC or rhodamine resistant to trypsin cleavage then, upon desuccinylation, the lysine/dye amide bond would become cleavable by trypsin. Note that removal of a single succinyl group from 2, followed by cleavage of the desuccinylated lysine would yield a compound with a single free amino function, Ac-K(Succ.)-R110. Monoamides of rhodamine 110 also have increased fluorescence emission at 530 nm relative to 2, although they are less fluorescent than rhodamine 110 itself (Liu et al., 1999). Thus, monitoring the fluorescence at the peak wavelength of the amino form of the dye would allow the desuccinylation reaction to be quantified. A schematic for such an assay is depicted for Compound 1 and SIRT5 in FIG. 1. The efficacy of trypsin for use in the second step of such an assay is demonstrated by the data presented in FIG. 2. Trypsin treatment (2 mg/ml) elicits an immediate increase in the fluorescence of a solution of Ac-Lys-AMC (Compound 6—FIG. 1) at the excitation and emission wavelengths of free AMC (Ex. 360 nm; Em. 460 nm), with maximum fluorescence achieved in 2 min. or less and ~⅔ of that maximum occurring in 1 min. (FIG. 2). In contrast, when Ac-Lys(Succ.)-AMC (1) is subjected to the same trypsin treatment, no change in fluorescence is observed over the entire course of the fluorescence measurement.

Figure 2:
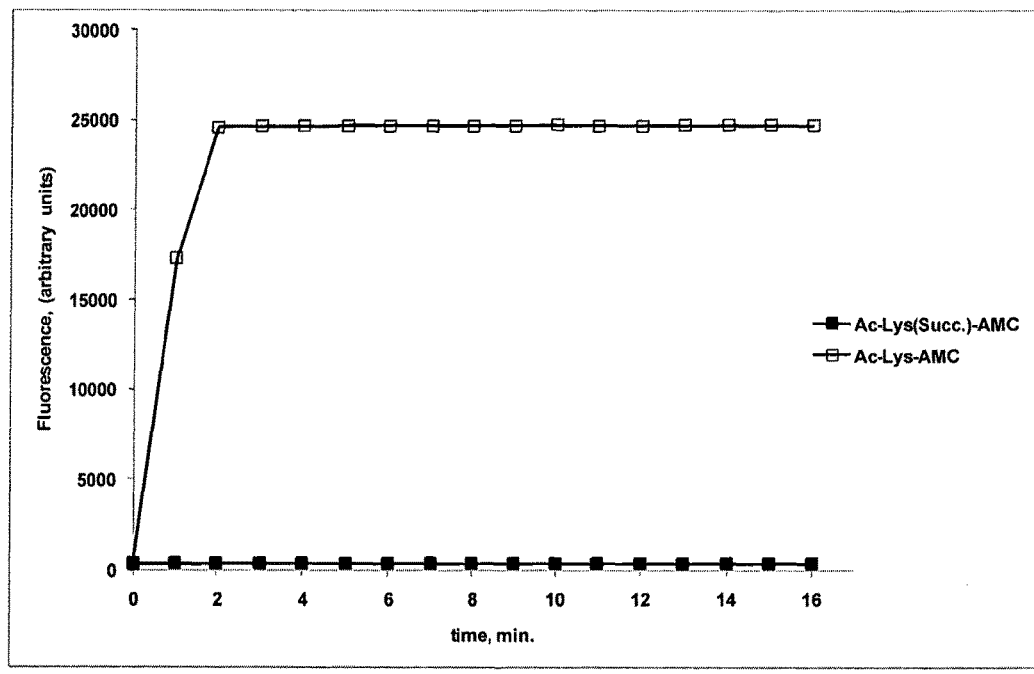
FIG. 2 is a graph showing that trypsin treatment releases fluorescent AMC from Ac-Lys-AMC but not Ac-Lys(Succinyl)-AMC. Samples (100 μl) of 1 μM Ac-Lys-AMC and 1 μM Ac-Lys(Succinyl)-AMC in a buffered solution (50 mM Tris/HCl, pH 8.0, 137 mM NaCl, 2.7 mM KCl, 1 mM MgCl$_2$) were treated with bovine pancreatic trypsin (2 mg/ml) for the indicated times at room temperature. Samples were in the wells of a 96-well, ½-area white microplate and fluorescence was measured at 1 min. intervals at the excitation and emission wavelengths for free AMC (Excitation: 360 nm; Emission: 460 nm) in a Synergy 2 microplate reading fluorimeter (BioTek), Gain 40. The data points at 0 min. represent the fluorescence of equivalent 1 μM Ac-Lys(Succ.)-AMC and 1 μM Ac-Lys-AMC samples in the absence of trypsin.
Figure 3:
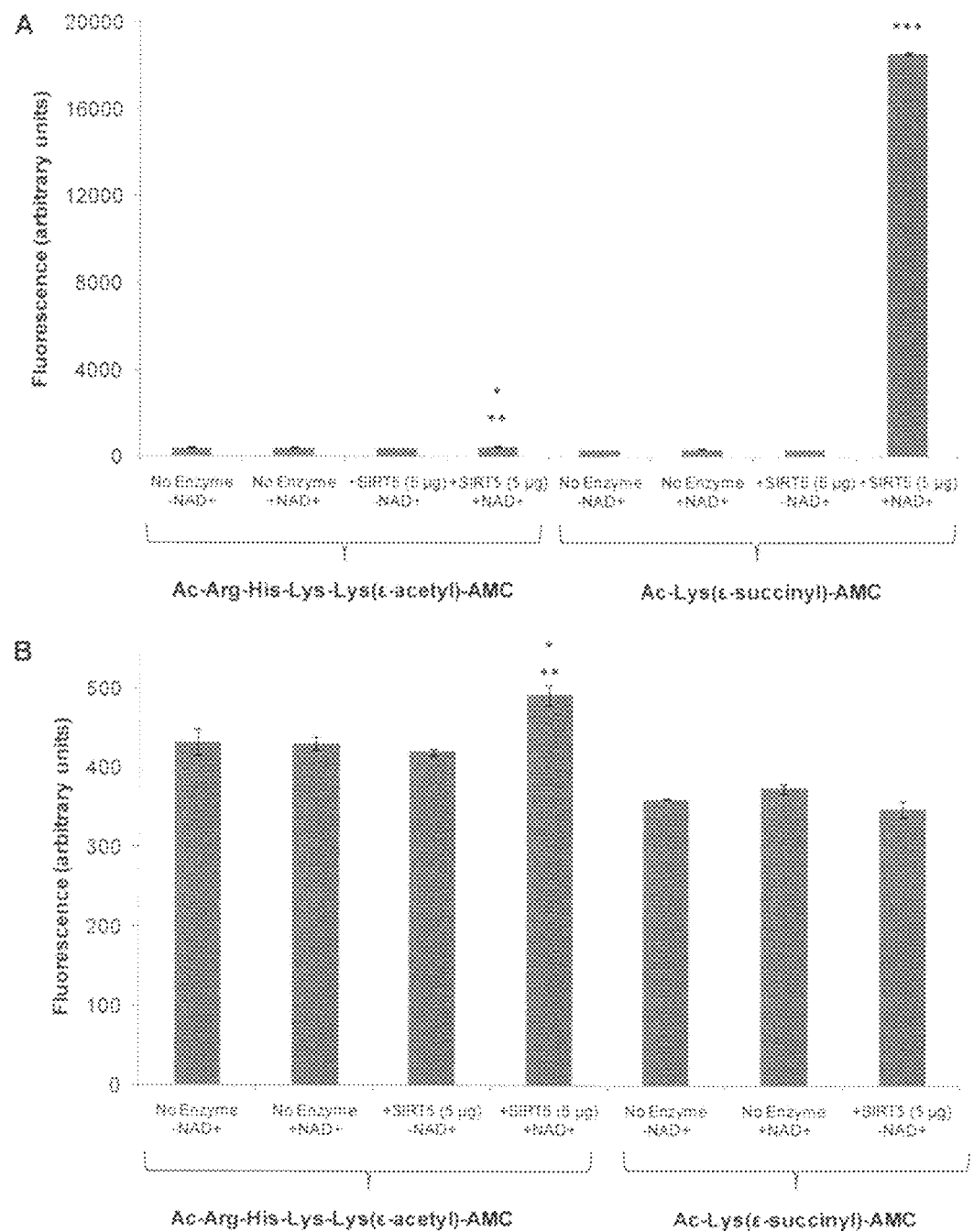
FIG. 3 is graphs showing that SIRT5 catalyzes NAD$^+$-dependent desuccinylation of Ac-Lys(ε-succinyl)-AMC far more efficiently than NAD$^+$-dependent deacetylation of Ac-Arg-His-Lys-Lys(ε-acetyl)-AMC. Fifty μl reactions in Assay Buffer (50 mM Tris/HCl, pH 8.0, 137 mM NaCl, 2.7 mM KCl, 1 min MgCl$_2$, 1 mg/ml BSA) included 50 μM of either Ac-Lys(ε-succinyl)-AMC or Ac-Arg-His-Lys(ε-acetyl)-AMC, and, where indicated, 500 μM NAD$^+$ and 5 μg recombinant human SIRT5 (Enzo Life Sciences Cat. #BML-SE555). After 60 min. at 37° C., reactions were stopped and AMC cleaved from deacetylated/desuccinylated substrate by addition of 50 μl of "Developer" (4 mg/ml trypsin, 2 mM nicotinamide in Assay Buffer). AMC fluorescence was read in a Cytofluor II plate-reading fluorimeter (Perseptive Biosystems) at wavelengths 360 nm (excitation)/460 nm (emission), Gain 54. Data represent the mean of two (No Enzyme) or three (+SIRT5) determinations and error bars the standard deviations. Panels A and B present the same data, but with the +SIRT5/+NAD$^+$/Ac-Lys(ε-succinyl)-AMC bar omitted from B to show the detail on the remaining bars. Statistically significant differences (Student's t-test) are indicated by asterisks as follows: *: p<0.02 vs. corresponding No Enzyme control; : p<0.001 vs. corresponding –NAD$^+$ control; *: p<3×10$^{-6}$ vs. both No Enzyme and –NAD$^+$ controls.
Figure 5:
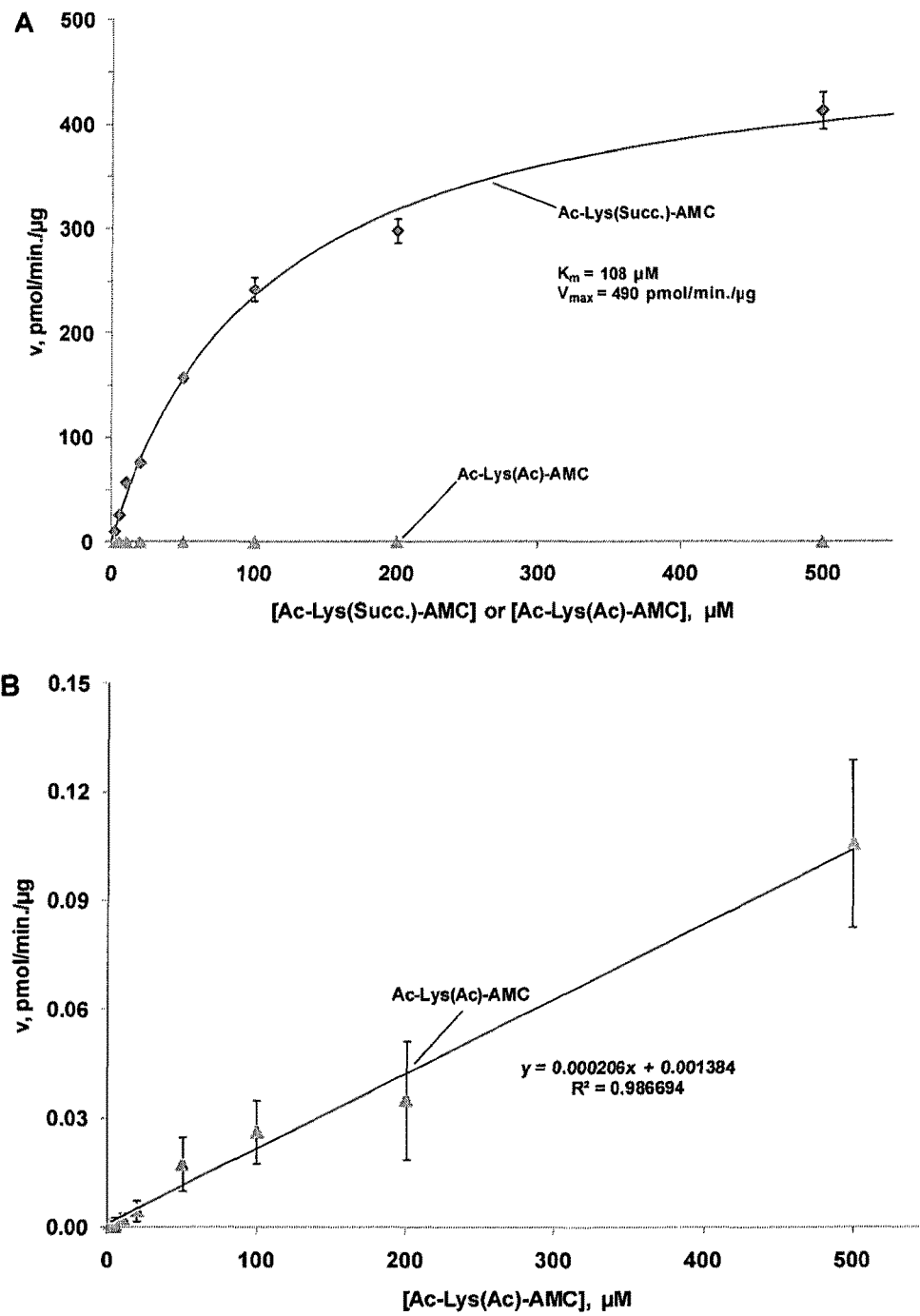
FIG. 5 is graphs showing dependence of SIRT5 initial rate kinetics on the concentrations of Ac-Lys(Succ.)-AMC and Ac-Lys(Ac.)-AMC. Fifty μl desuccinylation or deacetylation reactions were performed as described earlier (FIG. 4), with the indicated concentrations of Ac-Lys(Succ.)-AMC or Ac-Lys(Ac.)-AMC and 1 mM NAD$^+$, for 20 min. at 37° C. Reactions with Ac-Lys(Succ.)-AMC contained 10 ng SIRT5 and those with Ac-Lys(Ac.)-AMC contained 5 μg SIRT5. Reactions were stopped and AMC cleaved from deacetylated or desuccinylated substrate by trypsin treatment as described earlier (FIG. 4). AMC fluorescence was read in a Synergy 2 plate-reading fluorimeter (BioTek) at wavelengths 360 nm (excitation)/460 nm (emission), Gain 40. Data represent the mean of the differences of three determinations with enzyme (10 ng or 5 μg SIRT5) from the mean of two no enzyme samples for each substrate concentration. Error bars are the standard deviations from those means. Fluorescence differences were converted to specific activities (pmol/min/μg) by measuring the fluorescence increase due to the addition a standard solution of AMC (5 μl of a 3 μM solution=150 pmol). Panel A shows the curve for Ac-Lys.(Succ.)-AMC and kinetic parameters obtained from a non-linear least-squares fit to the Michaelis-Menten equation (Microsoft XL Solver tool). Panel B shows a the Ac-Lys(Ac.)-AMC data from Panel A with a 3333-fold expanded y-axis and a linear least-squares fit to the data.

As demonstrated above for Compound 1, succinylation of the 6-amino function of lysine confers complete resistance to the trypsin cleavage and release of the free dye group, which occurs in the otherwise identical, but non-succinylated Compound 6 (FIG. 1). Therefore, if SIRT5 is capable of catalyzing the desuccinylation of a compound such as 1, it should be possible to perform a desuccinylation assay by the two-step procedure depicted in FIG. 1. However, SIRT5 desuccinylation activity with a single-lysine substrate such as compound 1 is by no means a certainty. While the activity of SIRT5 with the acetylated four residue peptide lysine substrate, Ac-Arg-His-Lys-Lys($\epsilon$-acetyl)-AMC is exceedingly weak (Nakagawa, T. et al., 2009), its activity with the single-lysine acetylated substrate, Ac-Lys($\epsilon$-acetyl)-AMC, is considerably worse (FIG. 5 and Table 2, further discussed below). Genuine SIRT5 desuccinylation activity with Ac-Lys($\epsilon$-succinyl)-AMC should of course depend on the presence of SIRT5, but also on the presence of the sirtuin co-substrate, NAD$^+$. A trial SIRT5 assay was conducted with Ac-Lys($\epsilon$-succinyl)-AMC under high enzyme concentration conditions (5 μg SIRT5 per 50 μl reaction) necessary for detection of SIRT5 deacetylation activity with Ac-Arg-His-Lys-Lys($\epsilon$-acetyl)-AMC (FIG. 3). Desuccinylation of Ac-Lys($\epsilon$-succinyl)-AMC was not only entirely dependent on the presence of SIRT5 and NAD$^+$ but was, moreover, at least 250-fold greater than the deacetylation of Ac-Arg-His-Lys-Lys($\epsilon$-acetyl)-AMC.

Figure 4:
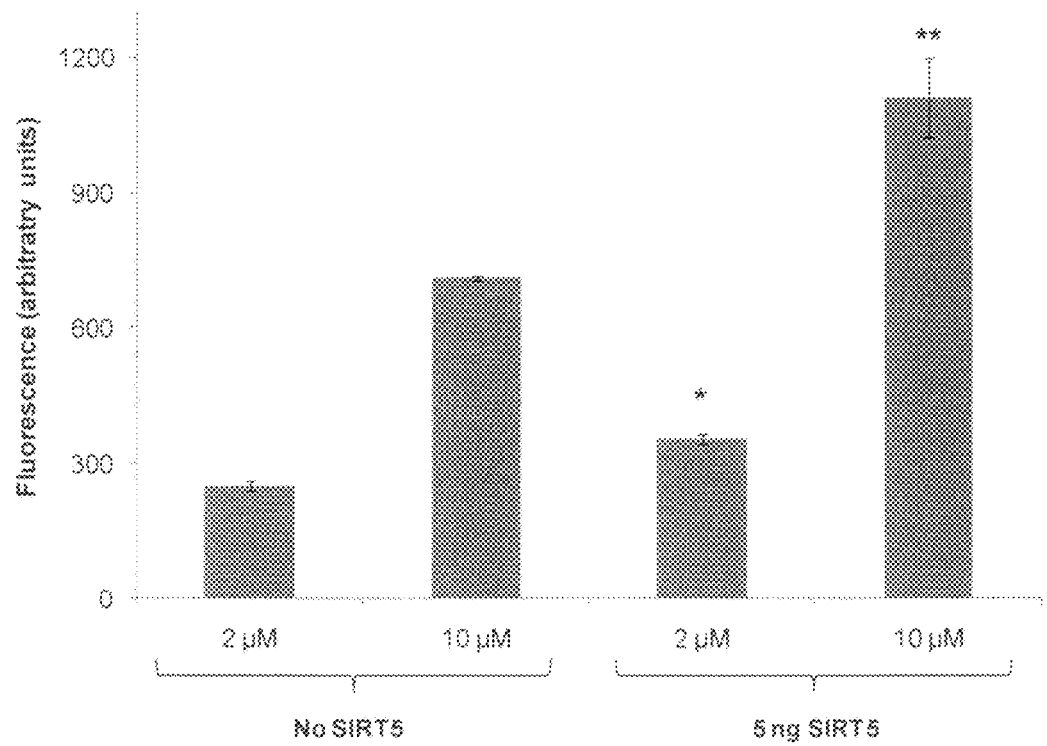
FIG. 4 is a graph showing that Ac-Lys(Succ.)-AMC enables SIRT5 assay at low enzyme concentrations. Fifty μl reactions in Assay Buffer (50 mM Tris/HCl, pH 8.0, 137 mM NaCl, 2.7 mM KCl, 1 mM MgCl$_2$, 1 mg/ml BSA) included 2 or 10 μM Ac-Lys(ε-succinyl)-AMC, 500 μM NAD$^+$ and, where indicated, 5 ng recombinant human SIRT5 (Enzo Life Sciences Cat. #BML-SE555). After 20 min. at 37° C., reactions were stopped and AMC cleaved from deacetylated/desuccinylated substrate by addition of 50 μl of "Developer" (4 mg/ml trypsin, 2 mM nicotinamide in Assay Buffer). AMC fluorescence was read in a Synergy 2 plate-reading fluorimeter (BioTek) at wavelengths 360 nm (excitation)/460 nm (emission), Gain 40. Data represent the mean of two (No Enzyme) or three (5 ng SIRT5) determinations and error bars the standard deviations. Statistically significant differences (Student's t-test) are indicated by asterisks as follows: *: p=0.002; **: p=0.009, each with respect to the corresponding "No SIRT5" samples.

As seen in FIG. 3, SIRT5 desuccinylated Ac-Lys(Succ.)-AMC far more efficiently than it deacetylated Ac-Arg-His-Lys-Lys($\epsilon$-acetyl)-AMC, a substrate which had, heretofore, been the most effective SIRT5 fluorogenic substrate known (U.S. Patent Application Publication 20060014705; Schlicker et al., 2008). In the FIG. 3 assays, 5 μg of SIRT5 (3 μM in 50 μl), 50 μM peptide substrate and a 60 min. incubation were used in order to achieve significant deacetylation of Ac-Arg-His-Lys-Lys($\epsilon$-acetyl)-AMC. Under these conditions nearly 50% of the Ac-Lys(Succ.)-AMC had been desuccinylated, so the SIRT5/NAD$^+$-dependent fluorescence increase would significantly underestimate the initial desuccinylation rate and the kinetic capacity of SIRT5 with Ac-Lys(Succ.)-AMC substrate. When assayed with lower quantities of SIRT5, lower Ac-Lys(Succ.)-AMC concentrations. and a shorter incubation time, statistically significant desuccinylation is achieved with 5 ng SIRT5/50 µl (3 nM), 2 or 10 µM Ac-Lys(Succ.)-AMC and a 20 min. incubation (FIG. 4). As noted in the Background of the Invention section, an assay's lower limit for determination of an inhibitor's $IC_{50}$ is one-half the enzyme concentration. Thus, an assay based on Ac-Lys(Succ.)-AMC, as opposed to an acetylated fluorogenic substrate, enables at least a three orders of magnitude improvement in the ability to detect or characterize high-potency inhibitors.

SIRT5 initial rate desuccinylation kinetics were determined as a function of the concentration of Ac-Lys(Succ.)-AMC and were compared in this regard to the equivalent single-lysine acetylated substrate, Ac-Lys(ε-acetyl)-AMC (FIG. 5, Ac-Lys(Ac)-AMC). Aside from the vastly greater initial rates achieved with the succinylated substrate, it is notable that the Ac-Lys(Succ.)-AMC substrate displays saturation kinetics, allowing the determination of the Michaelis-Menten constants $K_m$ and $V_{max}$ ($K_m$=108 µM; $V_{max}$=490 pmol/min/µg; FIG. 5A), whereas the rate dependence on the concentration of Ac-Lys(Ac)-AMC remains linear over the concentration range of the assay (FIG. 5B). This result with Ac-Lys(Ac)-AMC is similar to the high and uncertain $K_m$ estimate for the substrate Ac-Arg-His-Lys-Lys(ε-acetyl)-AMC (8.9 mM in assay with a maximum substrate concentration of 5 mM—U.S. Patent Application Publication 20060014705) and is consistent with a greater SIRT5 binding affinity for substrates that are succinylated rather than acetylated on the ε-amino function of lysine. The ability to obtain enzyme kinetic constants with the substrate(s) and assay of the present invention has utility for SIRT5 research and related drug discovery efforts, enabling for example the calculation of intrinsic inhibitor constants ($K_i$s) as opposed to relative, assay-dependent constants such as the $IC_{50}$.

Figure 6:
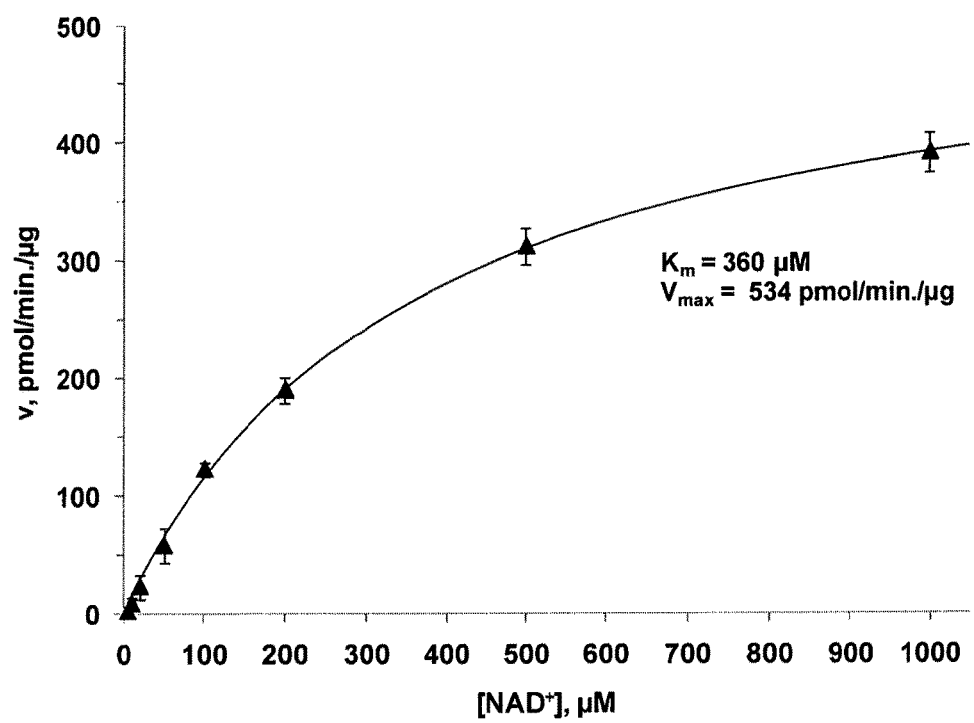
FIG. 6 is a graph showing the dependence of SIRT5 initial rate kinetics of Ac-Lys(Succ.)-AMC desuccinylation on the concentration of NAD$^+$. Reaction conditions were as described for FIG. 5 but with a constant Ac-Lys(Succ.)-AMC concentration of 0.5 mM and the indicated concentrations of NAD$^+$. Data analysis and determination of kinetic parameters were as described (FIG. 5).

SIRT5 kinetic parameters were also obtained for desuccinylation of a constant concentration of Ac-Lys(Succ.)-AMC (0.5 mM) as a function of the concentration of the cosubstrate $NAD^+$ (FIG. 6). The SIRT5/Ac-Lys(Succ.)-AMC kinetic parameters $k_{cat}$ and $k_{cat}/K_m$ were calculated from the data of FIG. 5 and the $NAD^+$ kinetic data of FIG. 6. These are listed in Table 1 along with literature values for human recombinant sirtuins with unlabeled acetylated lysine peptide substrates (histone H3 residues 1-20 or 4-15 acetylated on lysine-9 ("K9Ac")). It is notable that the $k_{cat}$ and $k_{cat}/K_m$ values for SIRT5 with Ac-Lys(Succ.)-AMC are similar to or in some cases greater than those of the bona fide sirtuin deacetylases SIRTs 1-3 with unlabeled acetylated peptide substrates.

A particularly important application of the present invention lies in the screening for and characterization of modulators (inhibitors or activators) of SIRT5 activity. The substrates provided may be used in homogenous assays. That is, the assays may be performed by a simple process of successive solution addition and mixing steps in a single vessel, for example the well of a microplate. As such, the assay may be easily adapted to automated liquid handling equipment and low-volume vessels (e.g. 96, 384 & 1536 well microplates) used, for example, in high-throughput screening of chemical libraries for modulators. High SIRT5 assay sensitivity is provided by the combination of the enzyme kinetic characteristics of the fluorophor-labeled succinylated-lysine substrates (FIGS. 3-6) and structures which allow trypsin-driven desuccinylation-dependent fluorescence increases (FIGS. 1 and 2). As noted earlier, this high sensitivity allows the use of low enzyme concentrations (e.g. 3 nM) in SIRT5 assays. Low enzyme concentrations are advantageous both for minimizing the costs of high-throughput screening and allowing the identification and characterization of high-potency modulators. To demonstrate the utility of the Ac-Lys(Succ.)-AMC substrate in characterizing SIRT5 inhibitors, two known SIRT5 inhibitors were chosen, suramin (U.S. Patent Application Publication 200600147050; Schuetz et al., 2007) and the general sirtuin inhibitor and reaction product nicotinamide. The data and calculations for determining their $IC_{50}$'s is shown in FIGS. 7 and 8. The suramin $IC_{50}$ obtained (27.3 µM; FIG. 7) agrees well with the value of 22 µM obtained in a radioactive assay with chemically acetylated chicken histones (Schuetz et al., 2007). The nicotinamide $IC_{50}$, under the same conditions, was 29.0 µM (FIG. 8). Nicotinamide is presumed to be a SIRT5 inhibitor, since, as is the case for other sirtuins, SIRT5 has nicotinamide-$NAD^+$ exchange activity (Schuetz et al., 2007). However, to our knowledge, no detailed characterization of SIRT5 inhibition by nicotinamide has been reported in the literature.

Since desuccinylation activity had not previously been attributed to any sirtuin (class III HDACs, i.e. $NAD^+$-dependent lysine deacetylases) or to any of the other, hydrolytic lysine deacetylases (class I, II and IV HDACs), it was investigated whether such activity was unique to SIRT5 and whether a substrate such as Compound 1 might form the basis of a SIRT5-specific assay. The Ac-Lys(Succ.)-AMC substrate was tested for activity with recombinant preparations of human HDACs 1-11, SIRTs 1-4, 6 and 7, a complex of HDAC3 with a fragment of the activating protein NCOR1 and with HeLa nuclear extract, a rich source of active

TABLE 1

Kinetic Parameters of Recombinant Human Sirtuins:
SIRT5 with Ac-Lys(Succ.)-AMC In Comparison to SIRTs 1-3, 5 with Acetylated Peptide Substrates

| Enzyme | Acetylated or Succinylated Lysyl Substrate | Varied Substrate | $K_m$ (Lysyl substrate) µM | $K_m$ ($NAD^+$) µM | $k_{cat}$ $s^{-1}$ | $k_{cat}/K_m$ $s^{-1}M^{-1}$ |
|---|---|---|---|---|---|---|
| SIRT5[a] | Ac-Lys(Succ.)-AMC | Lysyl | 108 | | 0.26 | 2450 |
| SIRT5[a] | Ac-Lys(Succ.)-AMC | $NAD^+$ | | 360 | 0.29 | 798 |
| SIRT1[b] | Hist. H3 4-15, K9Ac | $NAD^+$ | | 80 | 0.079 | 988 |
| SIRT2[b] | Hist. H3 4-15, K9Ac | $NAD^+$ | | 46 | 0.021 | 457 |
| SIRT2[c] | Hist. H3 1-20, K9Ac | Lysyl | 24 | | 0.24 | 10,000 |
| SIRT3[b] | Hist. H3 4-15, K9Ac | $NAD^+$ | | 118 | 0.009 | 76 |
| SIRT5[b] | Hist. H3 4-15, K9Ac | $NAD^+$ | | 861 | 0.003 | 3.5 |

[a]Data from present work, calculated from $K_m$ and $V_{max}$ values of FIGS. 7 and 8.
[b]Data from Du et al., 2009.
[c]Data from Borra et al., 2004.

HDACs in their native multiprotein complexes. No other sirtuin showed any activity with Ac-Lys(Succ.)-AMC (50 µM Ac-Lys(Succ.)-AMC, 500 µM NAD$^+$; Table 2). Extremely low, but detectable activities (Table 2; FIG. 9) were found for two class I HDACs (HDAC2 and HDAC3/NCOR1 complex) and for HeLa nuclear extract (ENZO Life Sciences Cat.#BML-KI142), a preparation rich in the class I HDACs 1, 2 and 3. For comparison, Table 2 includes the activities of all HDACs and SIRTs with the single-lysine substrate Ac-Lys(Ac)-AMC. The use of a longer peptide or otherwise modified (e.g., Lys(ε-trifluoroacetyl)) substrates, rather than Ac-Lys(Ac)-AMC, improves the activity of a number of HDACs and SIRTs. Examples of these activities are also included for comparison as "Other Substrates" (Table 2).

ground relative to SIRT5 activity include: 1) greater relative expression levels of the class I HDACs, 2) enhancement of class I HDAC activity when part of native multiprotein complexes (note the measurable activity of HDAC3/NCOR1 as opposed to the absence of activity from HDAC3), and 3) for intact cells and tissues, relative inaccessibility of SIRT5 to the substrate (native SIRT5 resides inside the mitochondrial inner membrane). The first two of these factors could readily be overcome by inclusion of an inhibitor, such as trichostatin A, which inhibits class I HDACs but not SIRTs (Bhalla et al., 2005).

An assay employing Ac-Lys(Ac.)-AMC to measure the HDAC and sirtuin deacetylase activity of intact cultured cells has been described (Howitz, K. T. et al. *Nature* 425, 191-196 (2003); Product Manual of Enzo Life Sciences Cat.

TABLE 2

Activities of Recombinant Human HDACs and Sirtuins with Ac-Lys(Succ.)-AMC, Ac-Lys(Ac.)-AMC and other Fluorigenic Substrates

| Enzyme | Activity with Ac-Lys(Succinyl)-AMC (pmol/min/µg)$^a$ | Activity with Ac-Lys(Acetyl)-AMC (pmol/min/µg)$^b$ | Other Substrates/ Activity (pmol/min/µg)$^c$ |
|---|---|---|---|
| HDAC1 | Undetectable (0.5 µg, 60 min.) | 14.8 | Ac-RHKK(Ac)-AMC/21 |
| HDAC2 | 0.28 | 554 | (Ac-Lys(Ac))$_2$-R110/502 |
| HDAC3 | Undetectable (0.5 µg, 60 min.) | 3.8 | |
| HDAC3/NCOR1 Complex | 0.40 | 668 | Ac-RHKK(Ac)-AMC/687 |
| HDAC4 | Undetectable (2 µg, 60 min) | Undetectable (2 µg, 60 min) | Ac-LGK(TFAc)-AMC/1390 |
| HDAC5 | Undetectable (2 µg, 60 min) | Undetectable (2 µg, 60 min) | Ac-LGK(TFAc)-AMC/9960 |
| HDAC6 | Undetectable (0.5 µg, 60 min.) | 1.0 | |
| HDAC7 | Undetectable (2 µg, 60 min) | Undetectable (2 µg, 60 min) | Ac-LGK(TFAc)-AMC/1670 |
| HDAC8 | Undetectable (0.5 µg, 60 min) | 0.091 | Ac-RHK(Ac)K(Ac)-AMC/4.5 |
| HDAC9 | Undetectable (2 µg, 60 min) | 0.027 | Ac-LGK(TFAc)-AMC/3330 |
| HDAC10 | Undetectable (0.3 µg, 60 min) | 1.21 | Ac-RHKK(Ac)-AMC/2.72 |
| HDAC11 | Undetectable (0.3 µg, 60 min) | 4.15 | Ac-RHKK(Ac)-AMC/6.09 |
| SIRT1 | Undetectable (1 µg, 60 min) | 0.391 | Ac-RHKK(Ac)-AMC/64 |
| SIRT2 | Undetectable (2.6 µg, 60 min) | 0.016 | Ac-QPKK(Ac)-AMC/18.6 |
| SIRT3 | Undetectable (3 µg, 60 min) | 0.125 | Ac-QPKK(Ac)-AMC/10.8 |
| SIRT4 | Undetectable (3 µg, 60 min) | Undetectable (3 µg, 60 min) | |
| SIRT5 | 115 | 0.0174 | Ac-RHKK(Ac)-AMC/0.364 |
| SIRT6 | Undetectable (3 µg, 60 min) | Undetectable (3 µg, 60 min) | Ac-RHKK(Ac)-AMC/0.052 |
| SIRT7 | Undetectable (3 µg, 60 min) | Undetectable (3 µg, 60 min) | |
| HeLa Nuclear Extract | 0.012 | 31 | |

$^a$Activities determined with 50 µM Ac-Lys(Succ.)-AMC (HDACs and SIRTs) with 500 µM NAD$^+$ added for SIRTs.
$^b$Activities determined with 50 µM Ac-Lys(Ac.)-AMC (HDACs and SIRTs) with 500 µM NAD$^+$ added for SIRTs.
$^c$Activities determined with 50 µM of indicated peptide substrates, single-letter amino acid code (HDACs and SIRTs) with 500 µM NAD$^+$ added for SIRTs. Substrate for the class IIa HDACs (4, 5, 7, 9) has trifluoroacetyl (TFAc) rather than acetyl function on the ε-amino group of lysine (Bradner, J. E. et al. *Nature Chem. Biol.* 6, 238-243 (2010)). The substrate Ac-Lys(Ac))$_2$-R110 (Enzo Life Science Cat. # BML-KI572, a component of Fluor de Lys-Green HDAC Assay Kit, Cat. #BML-AK530) is an analog of 2, but bears acetyl rather than succinyl functions.

The data of Table 2 and FIG. 9 indicate that, among human HDACs and SIRTs, desuccinylation activity with the substrate Ac-Lys(Succ.)-AMC (Compound 1) is nearly completely specific to SIRT5. Minor activity with class I HDACs could, however, contribute to a non-SIRT5 background in the context of assays on intact cells or tissues, or cell or tissue extracts. Factors which could increase this back-

BML-AK-503, "HDAC Fluorimetric Cellular Activity Assay Kit", Appendix F). Ac-Lys(Ac)-AMC is added to the culture medium, enters the cells and is deacetylated by HDACs and sirtuins in their native intracellular context. Measurement of the amount of Ac-Lys-AMC produced by intracellular deacetylation is then accomplished by detergent lysis of the cells and release of the AMC fluorophore by trypsin. We therefore investigated whether Ac-Lys(Succ.)-AMC could be used to measure intracellular desuccinylation activity, in a similar fashion, with cultured HeLa cells. However, as can be seen from FIG. 12A, no significant desuccinylation occurs after HeLa cells have been cultured four hours in the presence of 200 µM Ac-Lys(Succ.)-AMC. In contrast, a parallel set of HeLa cell treatments, with 200 µM Ac-Lys(Ac.)-AMC (FIG. 12B), produces significant deacetylation in four hours, the vast majority of which (>90%) is sensitive to the class I/II HDAC inhibitor trichostatin A (TSA). These latter, deacetylation results are consistent with previous observations made with this assay system (see Howitz, K. T. et al. Nature 425, 191-196 (2003) and Appendix F).

Aside from the far more limited range of enzymes capable of desuccinylating Ac-Lys(Succ.)-AMC, as opposed to deacetylating Ac-Lys(Ac.)-AMC (Table 2), another factor may be contributing to the lack of an intracellular desuccinylation signal (FIG. 10), namely the two membrane barriers (plasma and inner-mitochondrial membranes) standing between the medium and SIRT5. Absent a specific membrane transport protein, a molecule's membrane permeability (i.e. capacity to diffuse across the lipid bilayer) generally goes down with increasing size and with increasing polarity or charge (Stein, 1986). Since Ac-Lys(Succ.)-AMC is both larger than Ac-Lys(Ac.)-AMC (MW 445.5 vs. 387.4) and carries a negative charge, it is probable that its lower membrane permeability presents a greater kinetic barrier to diffusion across both the plasma and inner-mitochondrial membranes. Moreover, since Ac-Lys(Succ.)-AMC is negatively charged and since there is a negative inside membrane potential maintained across both of these membranes, the internal equilibrium concentration of the anionic Ac-Lys (Succ.)-AMC would likely be significantly lower than its external concentration (Johnson et al., 1981). This would in turn impose a kinetic constraint on a desuccinylating enzyme such as SIRT5.

In order to circumvent the problems likely imposed by these membrane barriers, whole HeLa cell lysates were prepared and tested for Ac-Lys(Succ.)-AMC desuccinylating activity (FIG. 11). Since the cells were lysed, the internal pool of the SIRT5 co-substrate $NAD^+$ was diluted into a much larger volume, allowing the effects of $NAD^+$'s presence or absence to be tested. It was also possible to use the membrane impermeant SIRT5 inhibitor suramin instead of nicotinamide. This has the advantage of avoiding possible complications resulting from metabolism of nicotinamide to $NAD^+$. Generalizations that can be drawn from this data include: 1) increases over the 2 hr. are dependent on the lysate since NL (No Lysate) fluorescences were approximately equal to the 0 hr. samples; 2) the maximum fluorescence increase (~22,000) over 0 hr./NL occurs in the absence of the class I/II HDAC inhibitor and the presence of $NAD^+$, indicating contributions both from sirloins (probably SIRT5) and non-sirtuin HDACs (probably class I); 3) consistent with point 2), the addition of TSA and the addition of suramin to the +$NAD^+$ condition each produce ~50% inhibition of the total 2 hr. fluorescence increase. This latter point is particularly interesting in that it suggests, despite the relative poor in vitro activity of the recombinant class I HDACs, that they may contribute levels of total cellular lysine-desuccinylating activity roughly comparable to those of SIRT5. Further, since the class I HDACs are primarily nuclear enzymes, it suggests that a proteomic investigation into the possible presence of lysine-succinylated proteins in that compartment may be warranted. Moreover, the apparent specificity, within the non-sirtuin HDACs, of the Ac-Lys (Succ.)-AMC substrate for the class I HDACs might provide information useful in the design of class I-specific inhibitors.

The results of the cell extract assays (FIG. 11) and SIRT5 kinetic studies suggest assay conditions for the measurement of SIRT5-specific desuccinylating activity in cell or tissue extracts or other mixed protein preparations (e.g. subcellular fractions such as isolated organelles, or partially purified cellular proteins such as chromatographic fractions). These conditions would simply be to determine the time-dependent increase in fluorescence (after trypsin release of AMC) in the presence of TSA (1 µM or higher), Ac-Lys(Succ.)-AMC (concentrations from 5 µM to 500 µM would be feasible) $NAD^+$ (concentrations from 30 µM to 3 mM would be feasible). A suitable control for such a measurement would be to also perform the assay in the absence of $NAD^+$. Note that in the presence of TSA, the withdrawal of $NAD^+$ eliminates the 0 to 2 hr. fluorescence increase (actually turns slightly negative but within the variability of the 0 hr. and No Lysate samples), thus confirming that the increase results from SIRT5 activity (compare fifth and second bars in FIG. 11B). An alternative means to determine the SIRT5 desuccinylation activity in a cell or tissue extract would be determine the total desucccinylation signal in the presence Ac-Lys(Succ.)-AMC and $NAD^+$ as above, but without TSA. The SIRT5 activity would then equal the decrease in of this time-dependent fluorescence change in the presence of a SIRT5 inhibitor. The inhibitor could be suramin (200 µM or higher) or nicotinamide (200 µM or higher).

The cell extract experiments of FIG. 11 were performed with 50 µM Ac-Lys(Succ.)-AMC and 500 µM $NAD^+$ (when present). These conditions were chosen to be the same as those of the survey of recombinant sirtuins and HDACs (Table 2) and, in the case of the 50 µM Ac-Lys(Succ.)-AMC, to minimize background fluorescence due to the substrate. Under these conditions, as noted above, TSA-sensitive activity (class I HDACs) contributed about half of the total desuccinylation in the absence of inhibitors. However, it should be possible to increase the SIRT5 portion of the total signal, particularly by increasing the $NAD^+$ concentration. Taking the $K_m$ for $NAD^+$ as 360 µM (FIG. 6), the Michaelis-Menten equation yields a result of 58% of $V_{max}$ at 500 µM. Increasing the $NAD^+$ concentration to 5 mM, for example, would increase the SIRT5 rate to 93% of $V_{max}$, while having no effect on the non-SIRT5 activity. The $K_m$'s of class I HDACs for Ac-Lys(Succ.)-AMC have not been determined, but given their low activity with this substrate it is likely that they are at least as high as that of SIRT5 (108 µM). Given that, below $K_m$, the enzyme velocity is roughly linear with substrate concentrations, the Ac-Lys(Succ.)-AMC could be lowered from 50 µM, thereby decreasing fluorescence background, while not decreasing the ratio of SIRT5 to class I HDAC activity.

It was possible with the HeLa lysate system to measure apparent SIRT5 Ac-Lys(Succ.)-AMC desuccinylating activity (FIG. 11) whereas this was not the case with intact HeLa cells (FIG. 10). Given that the cell number used in both assays were similar (equivalent of 28×10$^4$ for the cell extract vs. seeding at 4×10$^4$ per well and growth for ~20 hr. for the intact cells) and that the intact cell incubation was twice as long as that for the cell extracts, the membrane permeability factors discussed above are the most likely cause for this discrepancy. Chemical modifications to the Ac-Lys(Succ.)-AMC that render the distal carboxylate of the succinyl group neutral, rather than negative at neutral pH, could enable an intact cell assay that is capable of SIRT5 detection. Such modifications might include amidation and esterification. Acetoxymethyl (AM) esterification, which tends to be removed intracellularly by non-specific esterases, could improve the membrane permeability, while also allowing for restoration of the original substrate molecule within the cell.

Another example of a fluorogenic substrate for assay of SIRT5 desuccinylase activity is Compound 2 ((Ac-Lys (Succ.))$_2$-R110). The SIRT5 and NAD$^+$-dependent increase in fluorescence was determined for (Ac-Lys(Succ.))$_2$-R110 in comparison to that for deacetylase substrate (Ac-Lys (Ac.))$_2$-R110 (Fluor de Lys'-Green, Enzo Life Sciences Cat. #KI-572) and the data are shown in FIG. 12.

Figure 12:
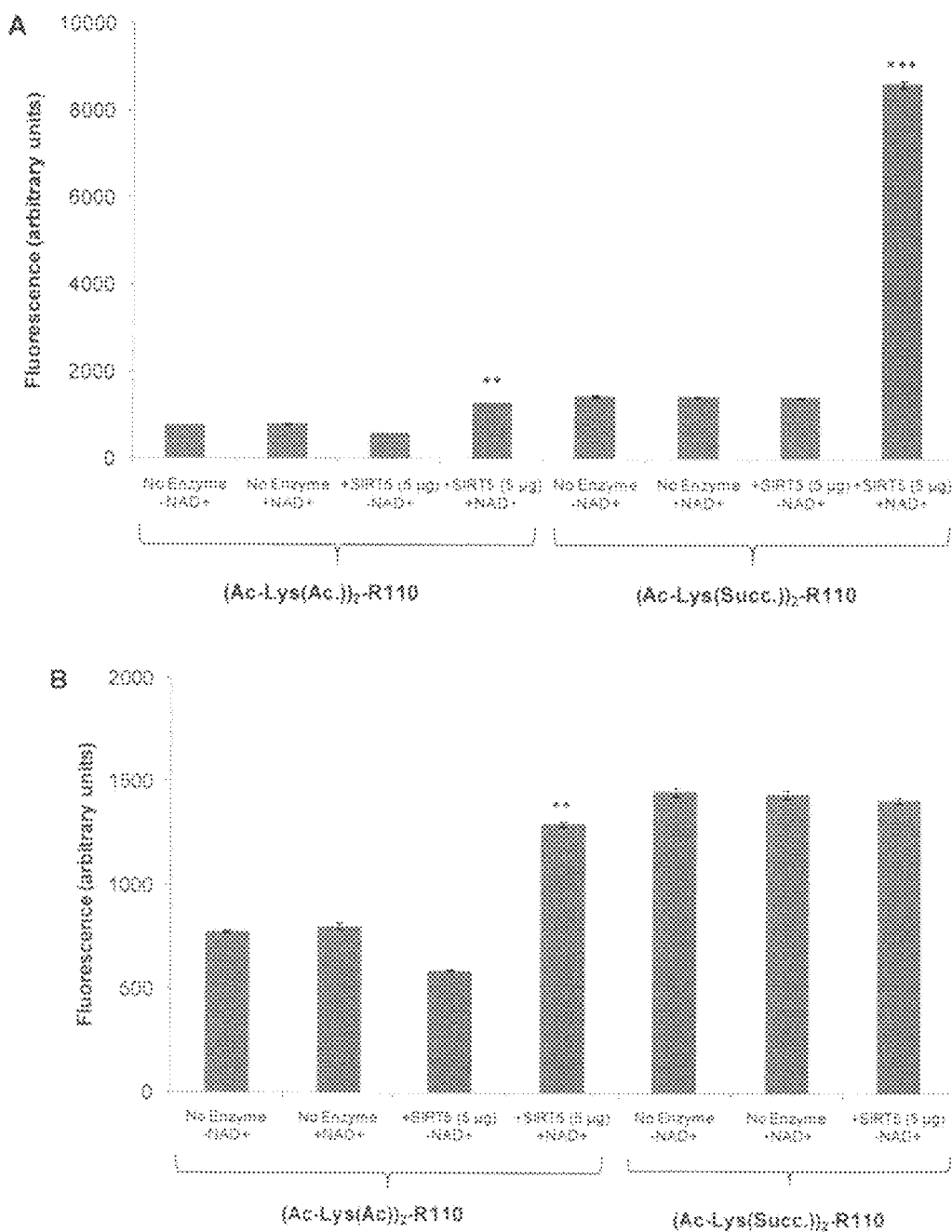
FIG. 12 is graphs showing that SIRT5 catalyzes NAD⁺-dependent desuccinylation of (Ac-Lys(Succ.))₂-R110 far more efficiently than NAD⁺-dependent deacetylation of (Ac-Lys(Ac.))₂-R110. Fifty μl reactions in Assay Buffer (50 mM Tris/HCl, pH 8.0, 137 mM NaCl, 2.7 mM KCl, 1 mM MgCl₂, 1 mg/ml BSA) included 50 μM of either (Ac-Lys (Succ.))₂-R110 or (Ac-Lys(Ac.))₂-R110, and, where indicated, 500 μM NAD⁺ and 5 μg recombinant human SIRT5 (Enzo Life Sciences Cat. #BML-SE555). After 60 min. at 37° C., reactions were stopped and the Ac-Lys cleaved from the R110 (rhodamine green) substrate by addition of 50 μl of "Developer" (4 mg/ml trypsin, 2 mM nicotinamide in Assay Buffer). Fluorescence was read in a Cytofluor II plate-reading fluorimeter (Perceptive Biosystems) at wavelengths 485 nm (excitation)/530 nm (emission), Gain 37. Data represent the mean of two (No Enzyme) or three (+SIRT5) determinations and error bars the standard deviations. Panels A and B present the same data, but with the +SIRT5/+NAD⁺/(Ac-Lys(Succ.))₂-R110 bar omitted from B to show the detail on the remaining bars. Statistically significant differences (Student's t-test) are indicated by asterisks as follows: : p<3×10⁻⁵ vs. corresponding +NAD⁺/No Enzyme control; *: p<2×10⁻⁶ vs. corresponding +NAD⁺/No Enzyme control.

As was the case for the Ac-Lys(Succ.)-AMC (FIG. 3), the (Ac-Lys(Succ.))$_2$-R110 substrate is desuccinylated by SIRT5 in a time and NAD$^+$-dependent manner (FIG. 12). Further, as was the case with Ac-Lys(Succ.)-AMC in comparison to Ac-Lys(Ac.)-AMC (Table 2), SIRT5 operates far more efficiently with the succinylated substrate.

Various HDAC enzymes, including SIRT1, 3, 6 and 7, were tested for activity with Compounds 4 (Ac-Lys(Myr.)-AMC) and 5 (Ac-Lys(Methyl Succ.)-AMC) to determine the lysyl-N$^\epsilon$de-myristoyl (Compound 4) and de-methylsuccinyl (Compound 5) activity of those enzymes. Results are shown in Table 3. As shown therein, some of those enzymes had activity with those reagents, although the activity was much lower than the activity with Ac-Lys(Acetyl)-AMC.

TABLE 3

Activities of Recombinant Human HDACs and Sirtuins with Ac-Lys(Myristoyl)-AMC, Ac-Lys(Methyl Succinyl)-AMC, Ac-Lys(Ac.)-AMC

| Enzyme | Activity with Ac-Lys(Myristoyl)-AMC (pmol/min/µg)$^a$ | Activity with Ac-Lys(Methyl Succinyl)-AMC (pmol/min/µg)$^a$ | Activity with Ac-Lys(Acetyl)-AMC (pmol/min/µg)$^b$ |
|---|---|---|---|
| HDAC1 | 1.651 | 0.798 | 14.8 |
| HDAC2 | 83.05 | 31.330 | 554 |
| HDAC3 | 0.963 | 0.431 | 3.80 |
| HDAC3/NCOR1 Complex | 79.023 | 53.750 | 668 |
| HDAC5 | Undetectable (2 µg, 60 min) | Undetectable (2 µg, 60 min) | Undetectable (2 µg, 60 min) |
| HDAC7 | Undetectable (2 µg, 60 min) | Undetectable (2 µg, 60 min) | Undetectable (2 µg, 60 min) |
| HDAC8 | Undetectable (0.5 µg, 60 min) | 0.003 | 0.091 |
| HDAC9 | Undetectable (2 µg, 60 min) | 0.135 | 0.027 |
| SIRT1 | 0.043 | 0.002 | 0.391 |
| SIRT3 | 0.012 | 0.002 | 0.125 |
| SIRT6 | 0.074 | 0.006 | 0.436 |
| SIRT7 | Undetectable (3 µg, 60 min) | Undetectable (3 µg, 60 min) | Undetectable (3 µg, 60 min) |
| HeLa Nuclear Extract | 0.819 | 1.764 | 31 |

$^a$Activities determined with 50 µM Ac-Lys(Succ.)-AMC (HDACs and SIRTs) with 500 µM NAD$^+$ added for SIRTs.
$^b$Activities determined with 50 µM Ac-Lys(Ac.)-AMC (HDACs and SIRTs) with 500 µM NAD$^+$ added for SIRTs.

Materials and Methods

Enzymes and Protein Extracts.

Enzyme and extract catalog products obtained from ENZO Life Sciences included: HDAC1 (Cat. #BML-SE456), HDAC2 (Cat. #BML-SE500), HDAC3 (Cat. #BML-SE507), HDAC3/NCOR1 Complex (Cat. #BML-SE515), HDAC6 (Cat. #BML-SE508), HDAC8 (Cat. #BML-SE145), HDAC10 (Cat. #BML-SE559), HDAC11 (Cat. #BML-SE560), SIRT1 (Cat. #BML-SE239), SIRT2 (Cat. #BML-SE251), SIRT3 (Cat. #BML-SE270), SIRT5 (Cat. #BML-SE555), HeLa Nuclear Extract (Cat. #BML-KI140), Trypsin ("Fluor de Lys Developer", 80 mg/ml bovine trypsin in 1 mM HCl, Cat. #BML-KI105 or "Fluor de Lys Developer II", 80 mg/ml bovine trypsin in 1 mM HCl, Cat. #BML-KI176). Enzymes produced internally at Enzo Life Sciences International, Plymouth Meeting, Pa. included: HDAC4 (human recombinant, residues 626-824 of GenBank accession #NP_006028 with an N-terminal His-tag (MGSSHHHHHHSSGLVPRGSHMAS, one-letter code), expressed in E. coli), HDAC5 (human recombinant, residues 657-1123 of GenBank accession #NP_001015053 with an N-terminal His-tag (MGSSHHHHHHSSGLVPRGSHMAS, one-letter code), expressed in E. coli), HDAC7 (human recombinant, residues 483-903 of GenBank accession #NP_056216 with an N-terminal His-tag (MGSSHHHHHHHSSGLVPRGSHMAS, one-letter code), expressed in E. coli), HDAC9 (human recombinant, residues 644-1066 of GenBank accession #NP_848510 with an N-terminal His-tag (MGSSHHHHHHSSGLVPRGSHMAS, one-letter code), expressed in E. coli). Enzymes obtained from BPS Bioscience, San Diego, Calif. included: human recombinants SIRT4 (Cat. #50015), SIRT6 (Cat. #50017), SIRT7 (Cat. #50018). HeLa whole cell extract was obtained from HeLa S3 cells (American Type Culture Collection) grown in a medium of MEM/10% fetal bovine serum (FBS) as follows: 1) 9×10$^6$ cells were suspended by trypsinization, followed by a phosphate buffered saline (PBS) rinse and addition of MEM/10% FBS (1.5 mL) to eliminate trypsin before transfer to a 15 mL conical tube; 2) cells were sedimented by a low speed centrifugation, gently resuspended in PBS and sedimented again and supernatant removed; 3) lysis was induced by resuspension in 0.8 mL 50 mM Tris/HCl, pH 8.0 with the non-denaturing detergent NP-40 (0.5%), placement on ice and brief vortexing every 5 min. for 30 mM.; 4) 100 µl of a concentrated salt solution in the same buffer was added in order to bring the final buffer composition to 50 mM Tris/Cl, pH 8.0, 137 mM NaCl, 2.7 mM KCl, 1 mM MgCl$_2$, 0.5% NP-40; 5) particulate matter was cleared by centrifugation and the cleared lysate supernatant transferred to a 1.5 mL Eppendorf tube and stored on ice until use in activity assays.

Reagents.

Enzyme assay reagents were components from either the "SIRT1 Fluorometric Drug Discovery Kit" from Enzo Life Sciences (ELS) (Cat. #BML-AK555) or the "HDAC Fluorimetric Cellular Activity Assay Kit" (ELS Cat. #BML-AK503) plus: "Fluor de Lys Substrate" (Ac-Lys(Ac.)-AMC; ELS Cat. #BML-KI104), trichostatin A (TSA) (ELS Cat. #BML-GR309-9090), "Fluor de Lys Deacetylated Standard" (Ac-Lys-AMC; ELS Cat. #BML-KI142); "Fluor de Lys-SIRT2 Deacetylase Substrate" (Ac-Gln-Pro-Lys-Lys (Ac)-AMC; ELS Cat. #BML-KI179), "Fluor de Lys-HDAC8 Deacetylase Substrate" (Ac-Arg-His-Lys-Lys(Ac)-AMC; ELS Cat. #BML-KI178), "Fluor de Lys-Green Substrate" ((Ac-Lys(Ac))$_2$-R110; ELS Cat. #BML-KI572); the class IIa HDAC substrate Ac-Leu-Gly-Lys(TFAc)-AMC (Bradner et al., 2010) synthesized at Enzo Life Sciences International, Exeter, UK.

Activity Assays with Enzymes and Protein Extracts.

Assays were performed at 37° C., according to the manufacturer's instructions for the "SIRT1 Fluorometric Drug Discovery Kit" from Enzo Life Sciences (ELS) (Cat. #BML-AK555), with exceptions described as follows. Where indicated in figures and text, SIRT1 enzyme was replaced with another enzyme or extract and the "Fluor de Lys-SIRT1 Substrate" (Ac-Arg-His-Lys-Lys(Ac)-AMC; ELS Cat. #BML-KI-177) was replaced with another acetylated, succinylated or trifluoroacetylated substrate. In assays with non-sirtuin enzymes (class I HDACs 1, 2, 3 and 8; class II enzymes HDACs 4-7, 9 and 10; class IV enzyme HDAC11) NAD$^+$ was omitted and the nicotinamide in the "Developer" (trypsin) solution was replaced with 1 µM TSA. In the HeLa cell extract experiments (FIG. 11), the "Developer" solutions were varied in order that the final inhibitor concentrations for all samples were suramin (200 µM) and TSA (1 µM).

Activity Assays with Intact HeLa Cells.

Assays (FIG. 10) were performed according to the manufacturer's instructions for the ""HDAC Fluorometric Cellular Activity Assay Kit" (ELS Cat. #BML-AK503), with exceptions described as follows. Where indicated the "Fluor de Lys Substrate" (Ac-Lys(Ac.)-AMC; ELS Cat. #BML-KI104) was replaced with Ac-Lys(Succ.)-AMC (1). The "Developer/Cell Lysis Buffer" solutions were varied in order that the final inhibitor concentrations for all samples were nicotinamide (1 mM) and TSA (1 µM).

REFERENCES

Bakhanashvili, M. et al. *Cell Death Differ.* 15, 1865-1874 (2008).
Benoiton, L. & Deneault, J. *Biochim. Biophys. Acta* 113, 613-616 (1966).
Bhalla, K. N. *J. Clin. Oncol.* 23, 3971-3993 (2005).
Blander, G. and Guarente, L. *Annu. Rev. Biochem.* 73, 417-435 (2004).
Bitterman, K. J. et al. *J. Biol. Chem.* 277, 45099-45107 (2002).
Borra, M. T. et al. *Biochemistry* 43, 9877-9887 (2004).
Bradner, J. E. et al. *Nature Chem. Biol.* 6, 238-243 (2010).
Brownlee, M. et al. *Diabetes* 32, 680-684 (1983).
Buck, S. W. et al. *J. Leukoc. Biol.* 75, 1-12 (2004).
Chen, D. et al. *Cancer Res.* 66, 3485-3494 (2006).
Cheng, Z. et al. *Mol. Cell. Proteomics* 8, 45-52 (2009).
Copeland, R. A. *Enzymes: A practical introduction to structure, mechanism and data analysis.* Wiley-VCH, NY, 2$^{nd}$ ed., (2000).
de Souza-Pinto, N. C. et al. *Oncogene* 23, 6559-6568 (2004).
Du, J. et al. *Biochemistry* 48, 2878-2890 (2009).
Enzo Life Sciences Instruction Manual for BML-AK500.
Enzo Life Sciences Instruction Manual for BML-AK530.
Enzo Life Sciences instruction manual for BML-AK555.
Enzo Life Sciences Product Information sheet/assay protocol for BML-SE555.
Frye, R. A. Biochem. Biophys. Res. Commun. 273, 793-798 (2000).
Gertz, M. and Steegborn, C. *Biochim. Biophys. Acta* 1804, 1658-1665 (2010).
Haigis, M. C. et al. *Cell* 126, 941-954 (2006).
Hodawadekar, S. C. and Marmorstein, R. *Oncogene* 26, 5528-5540 (2007).
Howitz, K. T. et al. *Nature* 425, 191-196 (2003).
Huang, J. et al. *Biochim. Biophys. Acta* 1804, 1645-1651 (2010)/
Hoffman, K. et al. *Nucleic Acids Res.* 27, 2057-2058 (1999).
Imai, S et al. *Nature* 403, 795-800 (2000).
Inglese, J. et al. *Assay Guidance Manual Version 5.0.* Eli Lilly & Co. and NIH Chemical Genomics Center (2008) at website ncgc.nih.gov/guidance/section4.html#determine-sar.
Jiang, T. et al. *Proc. Natl. Acad. Sci. USA* 104, 60-65 (2007).
Johnson, L. V. et al. *J. Cell Biol.* 88, 526-535 (1981).
Joys, T. M. & Kim, H. *Biochim. Biophys. Acta* 581, 360-362 (1979).
Kato, Y. and Osawa, T. *Arch. Biochem. Biophys.* 501, 182-7 (2010).
Kawai, Y. et al. *J. Lipid Res.* 47, 1386-1398 (2006).
Kim, S. C. et al. *Mol. Cell.* 23, 607-618 (2006).
Langley, E. et al. *EMBO J.* 21, 2383-2396 (2002).
Lin, H. "The Enzymatic Activity of Sirtuins: Beyond NAD-Dependent Deacetylation", Chemical Biology Discussion Group Seminar, New York Academy of Sciences, Jan. 25, 2010, at website nyas.org/events/Detail.aspx?cid=342d2995-92ab-4615-95b2-f55444c64c68.
Liszt, G. et al. *J. Biol. Chem.* 280, 21313-21320 (2005).
Liu, J. et al. *Bioorg. Med. Chem. Lett.* 9, 3231-3236 (1999).
Luo, J. et al. *Cell* 107, 137-48 (2001).
Mahlknecht, U. et al. *Cytogenet. Genome Res.* 112, 208-212 (2008).
Mahyar-Roemer, M. et al. *Oncogene* 23, 6226-6236 (2004).
Martinez, R. J. et al. *J. Bacteriol.* 109, 1239-1246 (1972).
Michishita, E. et al. *Mol. Biol. Cell* 16, 4623-4635 (2005).
Nakagawa, T. et al. *Cell* 137, 560-570 (2009).
Nakamura, Y. et al. *Biochem. Biophys. Res. Commun.* 366, 174-179 (2008).
North, B. J. et al. *Molecular Cell* 11, 437-444 (2003).
North, B. J. et al. *Methods* 36, 338-345 (2005).
Pantazis, P. & Bonner, W. M. *J. Biol. Chem.* 256, 4669-4675 (1981).
Pfister, J. A. et al. *PLOS One* 3, e4090 (2008).
Poncz, L. & Dearborn, D. G. *J. Biol. Chem.* 258, 1844-1850 (1983).
Rusche, L. et al. *Annu. Rev. Biochem.* 72, 481-516 (2003).
Schlicker, C. et al. *J. Mol. Biol.* 382, 790-801 (2008).
Shimazu, T. et al. *Mech. Ageing Dev.* 131, 511-516 (2010).
Schuetz, A. et al. *Structure* 15, 377-389 (2007).
Schultz, B. E. et al. *Biochemistry* 43, 11083-11091 (2004).
Schwer, B. et al. *Aging Cell* 8, 604-606 (2009).
Seely, J. H. & Benoiton, N. L. *Can. J. Biochem.* 48, 1122-1131 (1970).
Smith, J. S. et al. *Proc. Natl. Acad. Sci. USA* 97, 6658-6663 (2000).
Starai, V. J. et al. *Science* 298, 2390-2392 (2002).
Stein, W. D., pp. 69-112 of "Transport and Diffusion Across Cell Membranes", Academic Press, Orlando (1986).
Stevenson, F. T. et al. *J. Exp. Med.* 176, 1053-1062 (1992).
Stevenson, F. T. et al. *Proc. Natl. Acad. Sci. USA* 90, 7245-7249 (1993).
Tamai, K. et al. U.S. Pat. No. 7,033,778 (2006) U.S. Pat. No. 7,256,013 (2007).
Tanner, K. G. et al. *Proc. Natl. Acad. Sci. USA* 97, 14178-14182 (2000).
Tanny, J. C. and Moazed, D. *Proc. Natl. Acad. Sci. USA* 98, 415-420 (2001)).
Vaziri, H. et al. *Cell* 107, 149-59 (2001).
Watkins, P. A. et al. *J. Lipid Research* 48, 2736-2750 (2007).
Wisniewski, J. R. et al. *Mol. Cell. Proteomics* 6, 72-87 (2007).
Wisniewski, J. R. et al. *Nucleic Acids Res.* 36, 570-577 (2008).
Zhang, J. et al. *J. Biomol. Screening* 4, 67-73 (1999).
Zhao, K. et al. *J. Mol. Biol.* 337, 731-741 (2004).
Zhou, X et al. *Proc. Natl. Acad. Sci. USA* 98, 10572-10577 (2001).
PCT Patent Application No. PCT/US10/02494.
PCT Patent Application No. PCT/US10/02572.
U.S. Patent Application Publication 20060014705.

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A compound having the structure

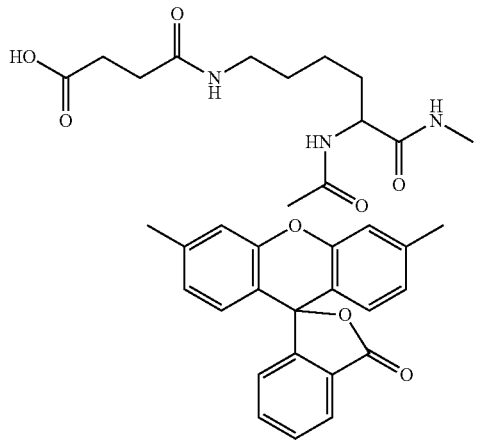

2. A compound having the structure

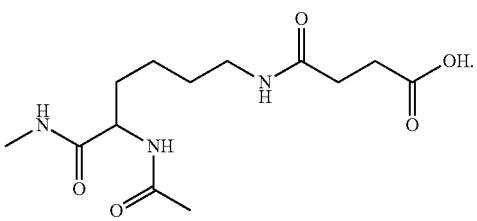

3. A compound having the structure

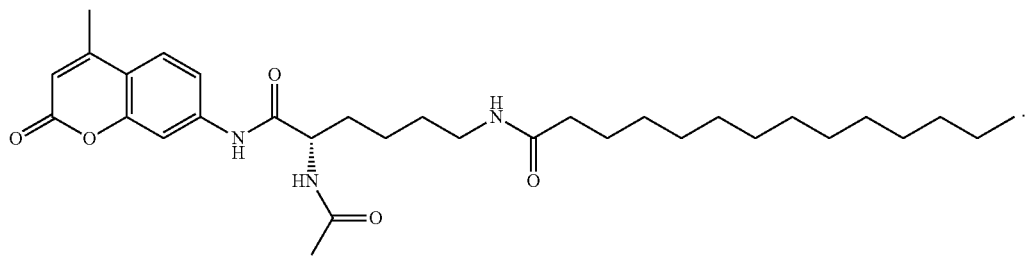 [SMILES: CCCCCCCCCCCCCC(=O)NCCCC[C@H](NC(C)=O)C(=O)Nc1ccc2c(C)cc(=O)oc2c1]

4. A compound having the structure

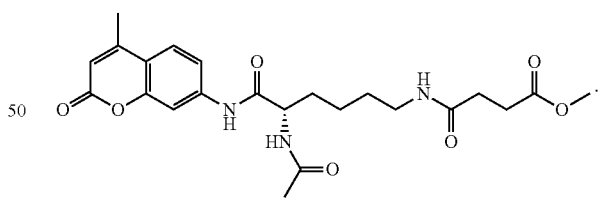

5. A compound having the structure

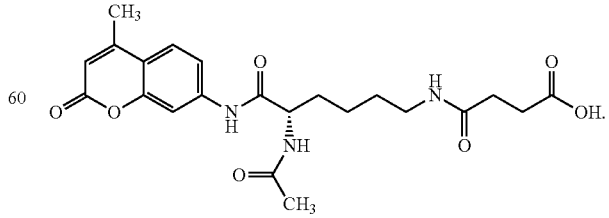

-continued

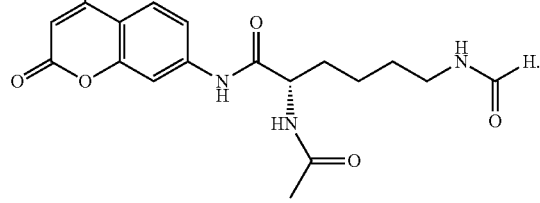

* * * * *

UNITED STATES PATENT AND TRADEMARK OFFICE
CERTIFICATE OF CORRECTION

Page 1 of 1

PATENT NO. : 9,637,773 B2
APPLICATION NO. : 12/930693
DATED : May 2, 2017
INVENTOR(S) : Konrad T. Howitz et al.

It is certified that error appears in the above-identified patent and that said Letters Patent is hereby corrected as shown below:

On the Title Page

Column 2, (57) ABSTRACT, two lines below the compound, add the word "moiety" after "myristoyl."

Column 2, (57) ABSTRACT, three lines below the compound, delete the words "is provided."

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*